US012805888B2

(12) United States Patent
Moosavi et al.

(10) Patent No.: US 12,805,888 B2
(45) Date of Patent: Nov. 24, 2026

(54) SYSTEMS, DEVICES, AND METHODS FOR SHOCK WAVE GENERATION UTILIZING CATHETERS WITH MULTI-METAL JOINTS

(71) Applicant: Shockwave Medical, Inc., Santa Clara, CA (US)

(72) Inventors: David Moosavi, Castro Valley, CA (US); Todd Weston Jenkins, San Jose, CA (US); Lawrence John Formosa, Campbell, CA (US); Danielle Sheree Rond, Santa Clara, CA (US); Rainier Betelia, San Jose, CA (US); Hoa D. Nguyen, San Jose, CA (US); Jason B. Franco, Milpitas, CA (US); Thomas Charles Hasenberg, Campbell, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 0 days.

(21) Appl. No.: 19/392,900

(22) Filed: Nov. 18, 2025

(65) Prior Publication Data

US 2026/0069299 A1 Mar. 12, 2026

Related U.S. Application Data

(62) Division of application No. 18/680,370, filed on May 31, 2024, now Pat. No. 12,502,188.

(51) Int. Cl.
*A61B 17/22* (2006.01)
*A61B 17/00* (2006.01)

(52) U.S. Cl.
CPC .. *A61B 17/22022* (2013.01); *A61B 17/00234* (2013.01); *A61B 2017/00172* (2013.01);
(Continued)

(58) Field of Classification Search
CPC .......... A61B 17/00234; A61B 17/2202; A61B 17/22022; A61B 2017/00172;
(Continued)

(56) References Cited

U.S. PATENT DOCUMENTS

| | | | |
|---|---|---|---|
| 2,916,647 | A | 12/1959 | George |
| 3,412,288 | A | 11/1968 | Ostrander |

(Continued)

FOREIGN PATENT DOCUMENTS

| | | | |
|---|---|---|---|
| AU | 2009313507 | B2 | 11/2014 |
| AU | 2013284490 | B2 | 5/2018 |

(Continued)

OTHER PUBLICATIONS

International Search Report and Written Opinion received for International Patent Application No. PCT/US2024/017293 mailed on Nov. 13, 2024, 11 pages.

(Continued)

*Primary Examiner* — Quang T Van

(74) *Attorney, Agent, or Firm* — Morrison & Foerster LLP

(57) ABSTRACT

A catheter includes a catheter body, a first conductive member including a first material positioned on the catheter body, a second conductive member including a second material different from the first material positioned on the catheter body, one or more electrical joints configured to electrically couple the first conductive member to the second conductive member, and one or more shock wave emitters. Each shock wave emitter is configured to generate a shock wave, and at least one shock wave emitter of the one or more shock wave emitters includes electrodes separated by a spark gap, in which at least one of the electrodes is formed from the second conductive member.

22 Claims, 8 Drawing Sheets

(52) U.S. Cl.
CPC ............... *A61B 2017/00238* (2013.01); *A61B 2017/00292* (2013.01); *A61B 2017/00477* (2013.01); *A61B 2017/00526* (2013.01); *A61B 2017/00836* (2013.01); *A61B 2017/00907* (2013.01); *A61B 2017/00929* (2013.01); *A61B 2017/00942* (2013.01); *A61B 2017/00946* (2013.01); *A61B 2017/00964* (2013.01); *A61B 2017/22025* (2013.01); *A61B 2017/22028* (2013.01)

(58) Field of Classification Search
CPC ........... A61B 2017/00238; A61B 2017/00292; A61B 2017/00477; A61B 2017/00526; A61B 2017/00836; A61B 2017/00907; A61B 2017/00929; A61B 2017/00942; A61B 2017/00946; A61B 2017/00964; A61B 2017/22015; A61B 2017/22025; A61B 2017/22028; A61B 2017/22062; C12Q 1/6827; C12Q 1/6853; C12Q 1/686; C12Q 1/6883; C12Q 2521/125; C12Q 2525/117; C12Q 2525/155; C12Q 2537/164; C12Q 2600/118; C12Q 2600/154
USPC ........ 219/603, 615, 616, 617, 633, 635, 659
See application file for complete search history.

(56) References Cited

U.S. PATENT DOCUMENTS 3,413,976 A 12/1968 Roze
3,524,101 A 8/1970 Barbini
3,583,766 A 6/1971 Padberg
3,785,382 A 1/1974 Schmidt-Kloiber et al.
3,902,499 A 9/1975 Shene
3,942,531 A 3/1976 Hoff et al.
4,027,674 A 6/1977 Tessler et al.
4,030,505 A 6/1977 Tessler
4,445,509 A 5/1984 Auth
4,662,126 A 5/1987 Malcolm
4,662,375 A 5/1987 Hepp et al.
4,671,254 A 6/1987 Fair
4,685,458 A 8/1987 Leckrone
4,741,405 A 5/1988 Moeny et al.
4,809,682 A 3/1989 Forssmann et al.
4,813,934 A 3/1989 Engelson et al.
4,878,495 A 11/1989 Grayzei
4,890,603 A 1/1990 Filler
4,900,303 A 2/1990 Lemelson
4,990,134 A 2/1991 Auth
4,994,032 A 2/1991 Sugiyama et al.
5,009,232 A 4/1991 Hassler et al.
5,046,503 A 9/1991 Schneiderman
5,057,103 A 10/1991 Davis
5,057,106 A 10/1991 Kasevich et al.
5,061,240 A 10/1991 Cherian
5,078,717 A 1/1992 Parins et al.
5,102,402 A 4/1992 Dror et al.
5,103,804 A 4/1992 Abele et al.
5,116,227 A 5/1992 Levy
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Muller et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,321,715 A 6/1994 Trost
5,324,255 A 6/1994 Passafaro et al.
5,336,234 A 8/1994 Vigil et al.
5,362,309 A 11/1994 Carter
5,364,393 A 11/1994 Auth et al.
5,368,591 A 11/1994 Lennox et al.
5,395,335 A 3/1995 Jang
5,417,208 A 5/1995 Winkler
5,425,735 A 6/1995 Rosen et al.
5,454,809 A 10/1995 Janssen
5,472,406 A 12/1995 de la Torre et al.
5,582,578 A 12/1996 Zhong et al.
5,584,843 A 12/1996 Wulfman et al.
5,603,731 A 2/1997 Whitney
5,609,606 A 3/1997 O'Boyle
5,662,590 A 9/1997 de la Torre et al.
5,709,676 A 1/1998 Alt
5,846,218 A 12/1998 Brisken et al.
5,891,089 A 4/1999 Katz et al.
5,893,840 A 4/1999 Hull et al.
5,931,805 A 8/1999 Brisken
6,007,530 A 12/1999 Dornhofer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster et al.
6,113,560 A 9/2000 Simnacher
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,398,792 B1 6/2002 O'Connor
6,406,486 B1 6/2002 de la Torre et al.
6,440,124 B1 8/2002 Esch et al.
6,494,890 B1 12/2002 Shturman et al.
6,514,203 B2 2/2003 Bukshpan
6,524,251 B2 2/2003 Rabiner et al.
6,589,253 B1 7/2003 Cornish et al.
6,607,003 B1 8/2003 Wilson
6,638,246 B1 10/2003 Naimark et al.
6,652,547 B2 11/2003 Rabiner et al.
6,666,834 B2 12/2003 Restle et al.
6,689,089 B1 2/2004 Tiedtke et al.
6,736,784 B1 5/2004 Menne et al.
6,740,081 B2 5/2004 Hilal
6,755,821 B1 6/2004 Fry
6,939,320 B2 9/2005 Lennox
6,989,009 B2 1/2006 Lafontaine
7,066,904 B2 6/2006 Rosenthal et al.
7,087,061 B2 8/2006 Chernenko et al.
7,241,295 B2 7/2007 Maguire
7,309,324 B2 12/2007 Hayes et al.
7,389,148 B1 6/2008 Morgan
7,505,812 B1 3/2009 Eggers et al.
7,569,032 B2 8/2009 Naimark et al.
7,850,685 B2 12/2010 Kunis et al.
7,853,332 B2 12/2010 Olsen et al.
7,873,404 B1 1/2011 Patton
7,951,111 B2 5/2011 Drasler et al.
8,162,859 B2 4/2012 Schultheiss et al.
8,177,801 B2 5/2012 Kallok et al.
8,353,923 B2 1/2013 Shturman
8,556,813 B2 10/2013 Cioanta et al.
8,574,247 B2 11/2013 Adams et al.
8,728,091 B2 5/2014 Hakala et al.
8,747,416 B2 6/2014 Hakala et al.
8,888,788 B2 11/2014 Hakala et al.
8,956,371 B2 2/2015 Hawkins et al.
8,956,374 B2 2/2015 Hawkins et al.
9,005,216 B2 4/2015 Hakala et al.
9,011,462 B2 4/2015 Adams et al.

(56) References Cited

U.S. PATENT DOCUMENTS 9,011,463 B2 4/2015 Adams et al.
9,044,618 B2 6/2015 Hawkins et al.
9,044,619 B2 6/2015 Hawkins et al.
9,072,534 B2 7/2015 Hakala et al.
9,138,249 B2 9/2015 Adams et al.
9,198,825 B2 12/2015 Katragadda et al.
9,333,000 B2 5/2016 Hakala et al.
9,421,025 B2 8/2016 Hawkins et al.
9,433,428 B2 9/2016 Hakala et al.
9,522,012 B2 12/2016 Adams
9,642,673 B2 5/2017 Adams et al.
9,855,050 B2 1/2018 Lorenzo et al.
9,993,292 B2 6/2018 Adams et al.
10,039,561 B2 8/2018 Adams et al.
10,118,015 B2 11/2018 De La Rama et al.
10,149,690 B2 12/2018 Hawkins et al.
10,154,799 B2 12/2018 Van Der Weide et al.
10,159,505 B2 12/2018 Hakala et al.
10,206,698 B2 2/2019 Hakala et al.
10,517,620 B2 12/2019 Adams
10,517,621 B1 12/2019 Adams
10,555,744 B2 2/2020 Nguyen et al.
10,682,178 B2 6/2020 Adams et al.
10,702,293 B2 7/2020 Hawkins et al.
10,709,462 B2 7/2020 Nguyen et al.
10,959,743 B2 3/2021 Adams et al.
10,966,737 B2 4/2021 Nguyen
10,973,538 B2 4/2021 Hakala et al.
11,000,299 B2 5/2021 Hawkins et al.
11,020,135 B1 6/2021 Hawkins
11,076,874 B2 8/2021 Hakala et al.
11,337,713 B2 5/2022 Nguyen et al.
11,432,834 B2 9/2022 Adams
11,478,261 B2 10/2022 Nguyen
11,534,187 B2 12/2022 Bonutti
11,596,423 B2 3/2023 Nguyen et al.
11,596,424 B2 3/2023 Hakala et al.
11,602,363 B2 3/2023 Nguyen et al.
11,622,780 B2 4/2023 Nguyen et al.
11,696,799 B2 7/2023 Adams et al.
11,771,449 B2 10/2023 Adams et al.
11,779,363 B2 * 10/2023 Vo .................... A61B 17/22022
606/128
12,402,899 B2 9/2025 Hasenberg et al.
12,433,620 B2 10/2025 Rond et al.
12,502,188 B2 12/2025 Moosavi et al.
2001/0044596 A1 11/2001 Jaafar
2002/0045890 A1 4/2002 Celliers et al.
2002/0082553 A1 6/2002 Duchamp
2002/0177889 A1 11/2002 Brisken et al.
2003/0004434 A1 1/2003 Greco et al.
2003/0176873 A1 9/2003 Chernenko et al.
2003/0229370 A1 12/2003 Miller
2004/0006333 A1 1/2004 Arnold et al.
2004/0010249 A1 1/2004 Truckai et al.
2004/0044308 A1 3/2004 Naimark et al.
2004/0097963 A1 5/2004 Seddon
2004/0097996 A1 5/2004 Rabiner et al.
2004/0162508 A1 8/2004 Uebelacker
2004/0249401 A1 12/2004 Rabiner et al.
2004/0254570 A1 12/2004 Hadjicostis et al.
2005/0015953 A1 1/2005 Keidar
2005/0021013 A1 1/2005 Visuri et al.
2005/0059965 A1 3/2005 Eberl et al.
2005/0075662 A1 4/2005 Pedersen et al.
2005/0090888 A1 4/2005 Hines et al.
2005/0113722 A1 5/2005 Schultheiss
2005/0113822 A1 5/2005 Fuimaono et al.
2005/0171527 A1 8/2005 Bhola
2005/0228372 A1 10/2005 Truckai et al.
2005/0245866 A1 11/2005 Azizi
2005/0251131 A1 11/2005 Lesh
2006/0004286 A1 1/2006 Chang et al.
2006/0069424 A1 3/2006 Acosta et al.
2006/0074484 A1 4/2006 Huber
2006/0184076 A1 8/2006 Gill et al.
2006/0190022 A1 8/2006 Beyar et al.
2006/0221528 A1 10/2006 Li et al.
2007/0016112 A1 1/2007 Schultheiss et al.
2007/0088380 A1 4/2007 Hirszowicz et al.
2007/0129667 A1 6/2007 Tiedtke et al.
2007/0156129 A1 7/2007 Kovalcheck
2007/0239082 A1 10/2007 Schultheiss et al.
2007/0239253 A1 10/2007 Jagger et al.
2007/0244423 A1 10/2007 Zumeris et al.
2007/0250052 A1 10/2007 Wham
2007/0255270 A1 11/2007 Carney
2007/0282301 A1 12/2007 Segalescu et al.
2007/0299481 A1 12/2007 Syed et al.
2008/0097251 A1 4/2008 Babaev
2008/0188913 A1 8/2008 Stone et al.
2009/0041833 A1 2/2009 Bettinger et al.
2009/0227992 A1 9/2009 Nir et al.
2009/0230822 A1 9/2009 Kushculey et al.
2009/0247945 A1 10/2009 Levit et al.
2009/0254114 A1 10/2009 Hirszowicz et al.
2009/0299447 A1 12/2009 Jensen et al.
2010/0016862 A1 1/2010 Hawkins et al.
2010/0036294 A1 2/2010 Mantell et al.
2010/0094209 A1 4/2010 Drasler et al.
2010/0114020 A1 5/2010 Hawkins et al.
2010/0114065 A1 5/2010 Hawkins et al.
2010/0121322 A1 5/2010 Swanson
2010/0179424 A1 7/2010 Warnking et al.
2010/0286709 A1 11/2010 Diamant et al.
2010/0305565 A1 12/2010 Truckai et al.
2011/0034832 A1 2/2011 Cioanta et al.
2011/0118634 A1 5/2011 Golan
2011/0208185 A1 8/2011 Diamant et al.
2011/0257523 A1 10/2011 Hastings et al.
2011/0295227 A1 12/2011 Hawkins et al.
2012/0071889 A1 3/2012 Mantell et al.
2012/0095461 A1 4/2012 Herscher et al.
2012/0116289 A1 5/2012 Hawkins et al.
2012/0143177 A1 6/2012 Avitall et al.
2012/0157991 A1 6/2012 Christian
2012/0203255 A1 8/2012 Hawkins et al.
2012/0253358 A1 10/2012 Golan et al.
2013/0030431 A1 1/2013 Adams
2013/0041355 A1 2/2013 Heeren et al.
2013/0116714 A1 5/2013 Adams et al.
2013/0123694 A1 5/2013 Subramaniyan et al.
2013/0150874 A1 6/2013 Kassab
2013/0253622 A1 9/2013 Hooven
2014/0039513 A1 * 2/2014 Hakala ............. A61B 17/22022
606/128
2014/0046229 A1 2/2014 Hawkins et al.
2014/0214061 A1 7/2014 Adams et al.
2014/0257130 A1 9/2014 Cao et al.
2015/0320432 A1 11/2015 Adams
2016/0151081 A1 6/2016 Adams et al.
2016/0324534 A1 11/2016 Hawkins et al.
2017/0135709 A1 5/2017 Nguyen et al.
2017/0303946 A1 10/2017 Ku et al.
2017/0311965 A1 11/2017 Adams
2018/0116717 A1 5/2018 Taff et al.
2019/0150960 A1 * 5/2019 Nguyen ............. A61B 18/1492
2021/0085347 A1 3/2021 Phan et al.
2021/0085383 A1 3/2021 Vo et al.
2021/0236778 A1 8/2021 Kim et al.
2021/0338258 A1 11/2021 Hawkins et al.
2022/0015785 A1 1/2022 Hakala et al.
2022/0125453 A1 4/2022 Nguyen
2022/0240958 A1 8/2022 Nguyen et al.
2022/0287731 A1 9/2022 Tan et al.
2022/0287732 A1 9/2022 Anderson et al.
2023/0043475 A1 2/2023 Adams
2023/0107690 A1 4/2023 Nguyen
2023/0111020 A1 4/2023 Sweis et al.
2023/0165598 A1 6/2023 Nguyen et al.
2023/0190316 A1 6/2023 Nguyen
2023/0293197 A1 9/2023 Nguyen et al.
2023/0310073 A1 10/2023 Adams et al.
2023/0329731 A1 10/2023 Hakala et al.

(56) References Cited

U.S. PATENT DOCUMENTS

| | | | |
|---|---|---|---|
| 2023/0380849 A1 | 11/2023 | Adams et al. |
| 2025/0268617 A1 | 8/2025 | Rond et al. |
| 2025/0275782 A1 | 9/2025 | Hasenberg et al. |
| 2026/0000418 A1 | 1/2026 | Rond et al. |

FOREIGN PATENT DOCUMENTS

| | | | |
|---|---|---|---|
| CA | 2104414 | A1 | 2/1995 |
| CN | 1204242 | A | 1/1999 |
| CN | 1269708 | A | 10/2000 |
| CN | 1942145 | A | 4/2007 |
| CN | 101043914 | A | 9/2007 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| DE | 3038445 | A1 | 5/1982 |
| DE | 202006014285 | U1 | 12/2006 |
| EP | 0442199 | A2 | 8/1991 |
| EP | 0571306 | A1 | 11/1993 |
| EP | 623360 | A1 | 11/1994 |
| EP | 0647435 | A1 | 4/1995 |
| EP | 2253884 | A1 | 11/2010 |
| EP | 2362798 | B1 | 4/2014 |
| JP | S62-099210 | U | 6/1987 |
| JP | S62-275446 | A | 11/1987 |
| JP | H03-63059 | A | 3/1991 |
| JP | H06-125915 | A | 5/1994 |
| JP | H07-47135 | A | 2/1995 |
| JP | H08-89511 | A | 4/1996 |
| JP | H10-99444 | A | 4/1998 |
| JP | H10-314177 | A | 12/1998 |
| JP | H10-513379 | A | 12/1998 |
| JP | 2002538932 | A | 11/2002 |
| JP | 2004081374 | A | 3/2004 |
| JP | 2004357792 | A | 12/2004 |
| JP | 2005501597 | A | 1/2005 |
| JP | 2005095410 | A | 4/2005 |
| JP | 2005515825 | A | 6/2005 |
| JP | 2006516465 | A | 7/2006 |
| JP | 2007289707 | A | 11/2007 |
| JP | 2007532182 | A | 11/2007 |
| JP | 2008506447 | A | 3/2008 |
| JP | 2011513694 | A | 4/2011 |
| JP | 2011520248 | A | 7/2011 |
| JP | 2011524203 | A | 9/2011 |
| JP | 2011528963 | A | 12/2011 |
| JP | 2012505050 | A | 3/2012 |
| JP | 2012508042 | A | 4/2012 |
| JP | 2015525657 | A | 9/2015 |
| JP | 2015528327 | A | 9/2015 |
| JP | 6029828 | B2 | 11/2016 |
| JP | 6081510 | B2 | 2/2017 |
| WO | WO-1989011307 | A1 | 11/1989 |
| WO | WO-1996024297 | A1 | 8/1996 |
| WO | WO-1999000060 | A1 | 1/1999 |
| WO | WO-1999002096 | A1 | 1/1999 |
| WO | WO-2000056237 | A2 | 9/2000 |
| WO | WO-2004069072 | A2 | 8/2004 |
| WO | WO-2005099594 | A1 | 10/2005 |
| WO | WO-2005102199 | A1 | 11/2005 |
| WO | WO-2006006169 | A2 | 1/2006 |
| WO | WO-2006127158 | A2 | 11/2006 |
| WO | WO-2007088546 | A2 | 8/2007 |
| WO | WO-2007149905 | A2 | 12/2007 |
| WO | WO-2009121017 | A1 | 10/2009 |
| WO | WO-2009126544 | A1 | 10/2009 |
| WO | WO-2009136268 | A1 | 11/2009 |
| WO | WO-2009152352 | A2 | 12/2009 |
| WO | WO-2010014515 | A2 | 2/2010 |
| WO | WO-2010054048 | A2 | 9/2010 |
| WO | WO-2011006017 | A1 | 1/2011 |
| WO | WO-2011094111 | A2 | 8/2011 |
| WO | WO-2011143468 | A2 | 11/2011 |
| WO | WO-2012025833 | A2 | 3/2012 |
| WO | WO-2013059735 | A1 | 4/2013 |
| WO | WO-2014025397 | A1 | 2/2014 |
| WO | WO-2014025620 | A1 | 2/2014 |
| WO | WO-2015017499 | A1 | 2/2015 |
| WO | WO-2019099218 | A1 | 5/2019 |

OTHER PUBLICATIONS

International Search Report and Written Opinion received for International Patent Application No. PCT/US2024/032421 mailed on Feb. 20, 2025, 7 pages.
Non-Final Office Action received for U.S. Appl. No. 18/586,299, mailed on Feb. 10, 2025, 12 pages.
Notice of Allowance received for U.S. Appl. No. 18/586,299, mailed on Jun. 9, 2025, 8 pages.
Advisory Action received for U.S. Appl. No. 18/680,370, mailed on Apr. 3, 2025, 2 pages.
Examiner Interview Summary Record received for U.S. Appl. No. 18/680,370, mailed on Mar. 24, 2025, 2 pages.
Final Office Action received for U.S. Appl. No. 18/680,370, mailed on Jan. 31, 2025, 14 pages.
Non-Final Office Action received for U.S. Appl. No. 18/680,370, mailed on Oct. 1, 2024, 12 pages.
Office Action received for U.S. Appl. No. 18/680,370, mailed on Apr. 24, 2025, 16 pages.

* cited by examiner

SYSTEMS, DEVICES, AND METHODS FOR SHOCK WAVE GENERATION UTILIZING CATHETERS WITH MULTI-METAL JOINTS

CROSS-REFERENCE TO RELATED APPLICATIONS

This application is a Divisional of U.S. patent application Ser. No. 18/680,370, filed on May 31, 2024, the contents of which is hereby incorporated by reference in its entirety.

FIELD

The present disclosure relates generally to the field of medical devices and methods, and more specifically to shock wave catheter devices for treating calcified lesions in body lumens, such as calcified lesions and occlusions in vasculature and kidney stones in the urinary system.

BACKGROUND

A wide variety of catheters have been developed for treating calcified lesions, such as calcified lesions in vasculature associated with arterial disease. For example, treatment systems for percutaneous coronary angioplasty or peripheral angioplasty use angioplasty balloons to dilate a calcified lesion and restore normal blood flow in a vessel. In these types of procedures, a catheter carrying a balloon is advanced into the vasculature along a guide wire until the balloon is aligned with calcified plaques. The balloon is then pressurized (normally to greater than ten atmospheres (10 atm)), causing the balloon to expand in a vessel to push calcified plaques back into the vessel wall and dilate occluded regions of vasculature.

More recently, the technique and treatment of intravascular lithotripsy (IVL) has been developed, which is an interventional procedure to modify calcified plaque in diseased arteries. The mechanism of plaque modification is through use of a catheter having one or more acoustic shock wave generating sources located within a liquid that can generate acoustic shock waves that modify the calcified plaque. IVL devices vary in design with respect to the energy source used to generate the acoustic shock waves, with two exemplary energy sources being electrohydraulic generation and laser generation.

For electrohydraulic generation of acoustic shock waves, a conductive solution (e.g., saline) may be contained within an enclosure that surrounds electrodes, or can be flushed through a tube that surrounds the electrodes. The calcified plaque modification is achieved by creating acoustic shock waves within the catheter by an electrical discharge across the electrodes. The energy from this electrical discharge enters the surrounding fluid faster than the speed of sound, generating an acoustic shock wave. In addition, the energy creates one or more rapidly expanding and collapsing vapor bubbles that generate secondary shock waves. The shock waves propagate radially outward and modify calcified plaque within the blood vessels. For laser generation of acoustic shock waves, a laser pulse is transmitted into and absorbed by a fluid within the catheter. This absorption process rapidly heats and vaporizes the fluid, thereby generating the rapidly expanding and collapsing vapor bubble, as well as the acoustic shock waves that propagate outward and modify the calcified plaque. The acoustic shock wave intensity is higher if a fluid is chosen that exhibits strong absorption at the laser wavelength that is employed. These examples of IVL devices are not intended to be a comprehensive list of potential energy sources to create IVL shock waves.

The IVL process may be considered different from standard atherectomy procedures in that it cracks calcium but does not liberate the cracked calcium from the tissue. Hence, generally speaking, IVL should not require aspiration nor embolic protection. Further, due to the compliance of a normal blood vessel and non-calcified plaque, the shock waves produced by IVL do not modify the normal vessel tissue or non-calcified plaque. Moreover, IVL does not carry the same degree of risk of perforation, dissection, or other damage to vasculature as atherectomy procedures or angioplasty procedures using cutting or scoring balloons.

More specifically, catheters to deliver IVL therapy have been developed that include pairs of electrodes for electrohydraulically generating shock waves inside an angioplasty balloon. Shock wave devices can be particularly effective for treating calcified plaque lesions because the acoustic pressure from the shock waves can crack and disrupt lesions near the angioplasty balloon without harming the surrounding tissue. In these devices, the catheter is advanced over a guidewire through a patient's vasculature until it is positioned proximal to and/or aligned with a calcified plaque lesion in a body lumen. The balloon is then inflated with conductive fluid (using a relatively low pressure of two to four atmospheres (2-4 atm) so that the balloon expands to contact the lesion but is not an inflation pressure that substantively displaces the lesion. Voltage pulses can then be applied across the electrodes of the electrode pairs to produce acoustic shock waves that propagate through the walls of the angioplasty balloon and into the lesions. Once the lesions have been cracked by the acoustic shock waves, the balloon can be expanded further to increase the cross-sectional area of the lumen and improve blood flow through the lumen. Alternative devices to deliver IVL therapy can be within a closed volume other than an angioplasty balloon, such as a cap, balloons of variable compliancy, or other enclosure.

Conventional shock wave emitters may include electrodes formed from copper, or may include electrodes formed from a metal such as stainless steel that is electrically connected to a power source through copper wires. Copper electrodes and copper wires can be advantageous for a variety of reasons. For instance, the relatively high conductivity of copper compared to other possible electrode materials places relatively minimal strain on power systems used for shock wave generation. Additionally, the relatively low stiffness of copper provides for a flexible catheter, thus easing deliverability. However, electrodes formed from such ductile materials may degrade with repeated shock wave generation, leading to sonic output loss. Further, electrode degradation may produce micro-scale shrapnel causing device failure.

SUMMARY

Described herein are systems, devices, and methods for generating shock waves utilizing a catheter that includes one or more electrodes comprising a material that provides increased durability upon shock wave generation relative to other metals that can be used for electrodes (e.g., copper, stainless steel, etc.). An exemplary catheter may include a catheter body and at least two different conductive members positioned on the catheter body. A first conductive member may be formed from a first material, and a second conductive member may be formed from a second material different from the first material. The first and second conductive members may be electrically coupled to one another by one or more electrical joints. The catheter may include one or more shock wave emitters that include electrode pairs separated by a spark gap. At least one of the electrodes of the one or more of the shock wave emitters may be formed from the second conductive member.

The properties (e.g., conductivity, stiffness, length, width, etc.) of the first material, first conductive member, second material, and second conductive member may be based on one or more target properties of the catheter, such as the durability and flexibility of the catheter. In some examples, the first material may have a higher conductivity, lower stiffness, or both, compared to the second material. The first conductive member may be disposed along a first length of the catheter body (e.g., the majority of the length of the catheter body). The second conductive member may be positioned at least partially distally on the catheter body relative to the first conductive member and may extend along a second length of the catheter body. In some aspects, the first length of the first conductive member may be longer than the second length of the second conductive member. In some examples, the length, width, or both of the first conductive member may affect the overall stiffness of the catheter. The length and/or width of the first conductive member may be configured based on a target stiffness or flexibility of the catheter, for example. Disposing the first conductive member along a first length (e.g., more than 50%) of the catheter body may help with deliverability of the catheter within the body due to the relatively low stiffness of the first conductive member. In some examples, the length, width, or both of the second conductive member may affect the durability of the catheter and conductivity of the electrical signals generated by power supply systems utilized for shock wave generation. The length and/or width of the second conductive member may be configured based on a target conductivity or resistivity of the conductive members and/or power supply system, for example. In some aspects, the second material may have a lower conductivity, higher stiffness, or both compared to the first material. Disposing the second conductive member along a second length (e.g., less than 50%) of the catheter body may help with increased resilience to the stresses experienced during shock wave generation.

Also disclosed herein are methods for forming electrical joints that electrically couple the conductive members positioned on the catheter body. In some examples, the joints are formed by applying one or more combinations of pressure, heat, and electrical current to one or more of the conductive members to melt at least one of the conductive members to join the members together. In some examples, the joints may include a connector, a conductive adhesive, a soldered joint, a welded joint, a crimped joint, or any combination thereof.

According to an aspect, an exemplary catheter for use in a body lumen comprises: a catheter body; a first conductive member comprising a first material positioned on the catheter body; a second conductive member comprising a second material different from the first material positioned on the catheter body, wherein the second material comprises a higher resistivity relative to the first material; one or more electrical joints configured to electrically couple the first conductive member to the second conductive member; and one or more shock wave emitters configured to generate one or more shock waves, and wherein at least one shock wave emitter of the one or more shock wave emitters comprises electrodes separated by a spark gap, wherein at least one of the electrodes is formed from the second conductive member.

Optionally, the one or more electrical joints comprise a connector, a conductive adhesive, a soldered joint, a welded joint, a crimped joint, or any combination thereof. Optionally, the one or more electrical joints comprise a conductive interface layer comprising a material different from the first material and the second material positioned between and electrically coupled to the first conductive member and the second conductive member. Optionally, the one or more electrical joints are formed using tack welding, laser welding, crimping, wrapping stripped wires around each other, soldering, swagging, a conductive adhesive, ferrule pins, or a combination thereof. Optionally, the conductive adhesive comprises at least one of silver, carbon graphite, gold, diamond, copper, and aluminum. Optionally, the ferrule pins comprise at least one of copper, brass, silver, tin, and stainless steel. Optionally, the ferrule pins are plated with at least one of nickel plating and chromium plating. Optionally, the second conductive member is positioned distally relative to the first conductive member on the catheter body. Optionally, the first conductive member comprises a first conductive wire configured to conduct electricity to the second conductive member via the one or more electrical joints and the second conductive member comprises a second conductive wire configured to conduct electricity to at least one of the one or more shock wave emitters.

Optionally, the second material comprises at least one of a higher stiffness, a higher density, and a higher melting point relative to the first material. Optionally, the first material comprises a higher conductivity relative to the second material. Optionally, the first material comprises copper, and the second material comprises molybdenum, tungsten, rhodium, rhenium, tantalum, niobium, or a combination thereof. Optionally, at least a portion of the second conductive member is coated or plated with a coating or plating comprising the first material. Optionally, the coating or plating comprises a nickel-copper coating or plating. Optionally, the nickel-copper coating or plating comprises between zero to ten microns (0-10 μm) of nickel and between one hundred to two hundred microns (100-200 μm) of copper. Optionally, the coating or plating comprises between 0% and 5% nickel and between 100% and 95% copper.

Optionally, at least one of the electrodes of the at least one shock wave emitter comprises an emitter band surrounding at least a portion of the catheter body. Optionally, each of the electrodes of the at least one shock wave emitter is formed from the second material. Optionally, at least one of the electrodes of the at least one shock wave emitter comprises an exposed distal end of the second conductive member, wherein the second conductive member comprises an insulated wire.

According to an aspect, an exemplary method of forming a catheter comprising one or more electrical joints configured to electrically couple a first conductive member to a second conductive member comprises: securing a first conductive member comprising a first material to a catheter body; securing a second conductive member comprising a second material different from the first material to the catheter body at a location distal of the first conductive member on the catheter body; forming one or more electrical joints for electrically coupling and joining the first conductive member wire and the second conductive member.

Optionally, forming one or more electrical joints comprises: inserting the first conductive member into a connector; inserting the second conductive member into the connector; and crimping the connector to the first conductive member and the second conductive member. Optionally, the connector comprises a conductive cylinder or a ferrule pin. Optionally, the conductive cylinder or the ferrule pin comprises copper, brass, silver, tin, stainless steel, or a combination thereof.

Optionally, forming one or more electrical joints comprises: applying pressure to the first conductive member and the second conductive member; passing current through the first conductive member, the second conductive member, or both to generate heat; and melting at least one of the first conductive member and the second conductive member to join the first conductive member and the second conductive member together.

Optionally, the method comprises: flattening at least one of the first conductive member and the second conductive member. Optionally, the method comprises: flowing an inert gas over at least a portion of the first conductive member and the second conductive member. Optionally, applying pressure to the first conductive member and the second conductive member comprises clamping the first conductive member and the second conductive member.

Optionally, forming one or more electrical joints comprises: clamping the first conductive member and the second conductive member; and heating the first conductive member and the second conductive member to melt at least one of the first conductive member and the second conductive member to join the first conductive member and the second conductive member together. Optionally, heating the first conductive member and the second conductive member comprises using a laser. Optionally, forming one or more electrical joints comprises soldering the first conductive member to the second conductive member.

According to an aspect, an exemplary system for generating shock waves comprises: a shock wave energy generator; and a catheter comprising: a catheter body; a first conductive member comprising a first material positioned on the catheter body; a second conductive member comprising a second material different from the first material positioned on the catheter body, wherein the second material comprises a higher resistivity relative to the first material; one or more electrical joints configured to electrically couple the first conductive member to the second conductive member; and one or more shock wave emitters, each shock wave emitter configured to generate a shock wave, and wherein at least one shock wave emitter of the one or more shock wave emitters comprises electrodes separated by a spark gap, wherein at least one of the electrodes is formed from the second conductive member. Optionally, the shock wave energy generator is configured to deliver high voltage pulses to a shock wave emitter of the plurality of shock wave emitters, wherein the high voltage pulses are between three kilovolts (3 kV) and thirty kilovolts (30 kV). Optionally, the shock wave energy generator is configured to deliver high voltage pulses to a shock wave emitter of the plurality of shock wave emitters, wherein the high voltage pulses are ten kilovolts (10 kV). Optionally, the shock wave energy generator is configured to deliver voltage pulses at a rate of between ten hertz (10 Hz) and ten kilohertz (10 kHz). Optionally, the shock wave energy generator applies an alternating current to the electrodes to induce a change in the polarity of the electrodes.

In some embodiments, any one or more of the characteristics of any one or more of the systems, methods, and/or devices recited above may be combined, in whole or in part, with one another and/or with any other features or characteristics described elsewhere herein.

BRIEF DESCRIPTION OF THE FIGURES

The invention will now be described, by way of example only, with reference to the accompanying drawings, in which.

DETAILED DESCRIPTION

Figure 1:
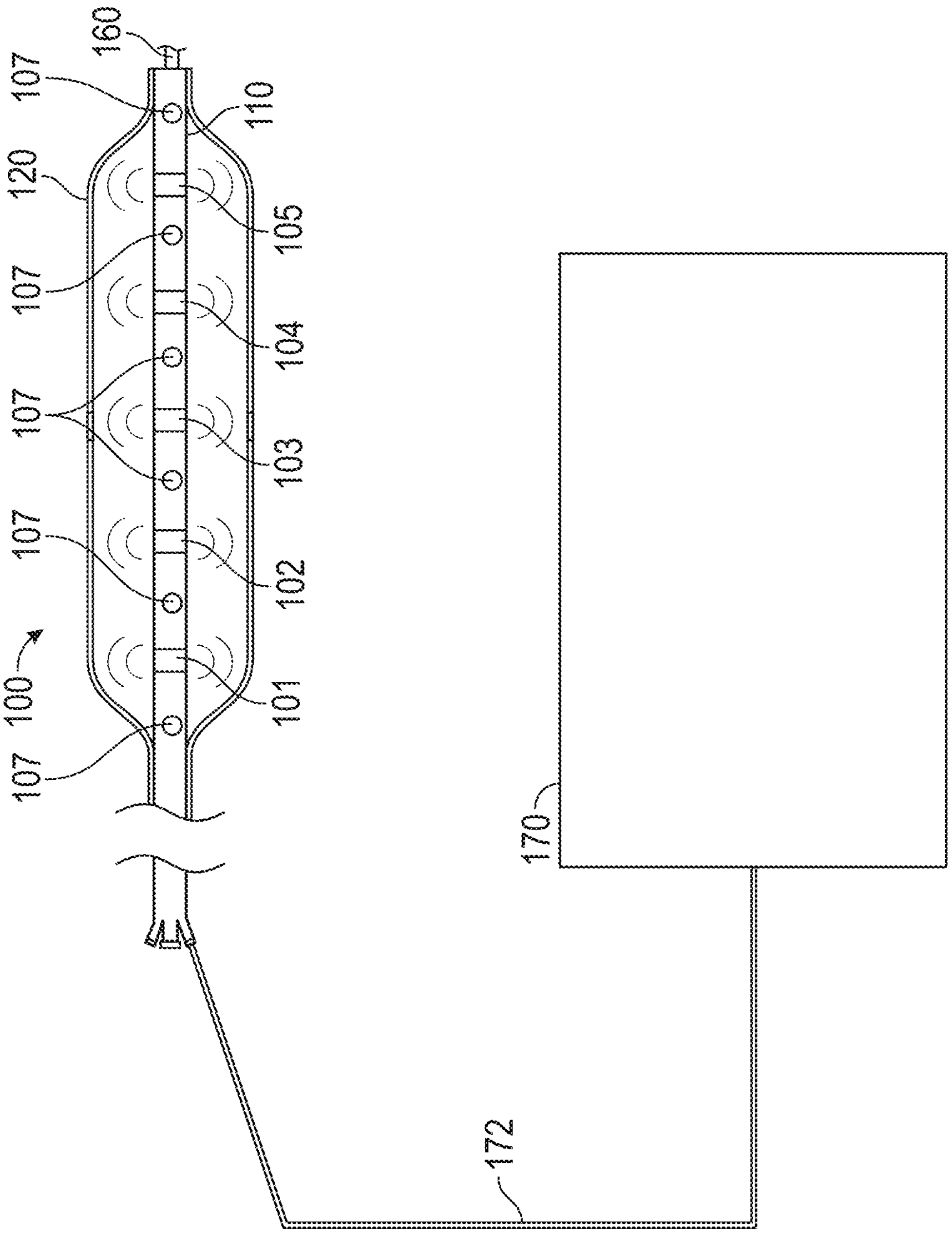
FIG. 1 illustrates an exemplary system for generating shock waves, according to some examples.

The following description is presented to enable a person of ordinary skill in the art to make and use the various embodiments and aspects thereof disclosed herein. Descriptions of specific devices, assemblies, techniques, and applications are provided only as examples. Various modifications to the examples described herein will be readily apparent to those of ordinary skill in the art, and the general principles described herein may be applied to other examples and applications without departing from the spirit and scope of the various embodiments and aspects thereof. Thus, the various embodiments and aspects thereof are not intended to be limited to the examples described herein and shown but are to be accorded the scope consistent with the claims.

Efforts have been made to improve the design of electrode assemblies included in shock wave and directed cavitation catheters. For instance, low-profile electrode assemblies have been developed that reduce the crossing profile of a catheter and allow the catheter to more easily navigate calcified vessels to deliver shock waves in more severely occluded regions of vasculature. Examples of low-profile electrode designs can be found in U.S. Pat. Nos. 8,888,788, 9,433,428, and 10,709,462, in U.S. Publication No. 2021/0085383, and in U.S. patent application Ser. No. 18/586,299, all of which are incorporated herein by reference in their entireties. Other catheter designs have improved the delivery of shock waves, for instance, by specific electrode construction and configuration thereby directing shock waves in a forward direction to break up tighter and harder-to-cross occlusions in vasculature. Examples of forward firing or forward-biased catheter designs can be found in U.S. Pat. Nos. 10,966,737, 11,478,261, and 11,596,423, in U.S. Publication Nos. 2023/0107690 and 2023/0165598, and in U.S. patent application Ser. No. 18/524,575, all of which are incorporated herein by reference in their entireties.

Disclosed herein are systems, devices, and methods for generating shock waves for the treatment of lesions within a body lumen. Exemplary catheters described herein may include a catheter body and one or more shock wave emitters configured to generate one or more shock waves. The one or more shock wave emitters may include electrodes separated by a spark gap (e.g., an electrode pair). At least two different conductive members may be respectively positioned on the catheter body. One conductive member (e.g., a second conductive member) may form an electrode of a shock wave emitter. Another conductive member (e.g., a first conductive member) may conduct one or more electrical signals to the electrode of the shock wave emitter. In some aspects, the second conductive member may not form an electrode of the shock wave emitter. The conductive members may comprise, at least in part, different materials having different properties (e.g., conductivity, stiffness, length, width), and may be electrically coupled together using one or more electrical joints.

The second material of the second conductive member (that forms an electrode of a shock wave emitter) may be configured with at least one of: a higher stiffness, a higher density, a higher melting point, and a higher resistivity, relative to the first material of the first conductive member (that does not form an electrode of a shock wave emitter). As a result, the second conductive member may be able to better withstand being subjected to high stresses during shock wave generation. In some examples, the second material of the second conductive member may be able to maintain sonic output during shock wave generation after at least 200 voltage pulses, at least 300 voltage pulses, and/or at least 400 voltage pulses. The first material of the first conductive member (that does not form an electrode of a shock wave emitter) may be disposed along a majority of the length of the catheter body given its relatively lower resistivity and lower stiffness. Such properties may ensure the catheter is adequately deliverable (e.g., having a stiffness lower than a stiffness threshold) within the body lumen and that sufficient current reaches the electrodes forming one or more shock wave emitters on the catheter. In some examples, the first material of the first conductive member (that does not form an electrode of a shock wave emitter) comprises copper. In some examples, the second material of the second conductive member (that does form a shock wave emitter) comprises molybdenum, tungsten, rhodium, rhenium, tantalum, niobium, chromium, or a combination thereof. In some examples, the second material of the second conductive member includes a refractory metal. In some examples, the second material has a melting point higher than one thousand eight hundred fifty degrees Celsius (1,850° C.). In some examples, the second conductive member is a superalloy. In some examples, the second conductive member is a nickel-chromium alloy. In some examples, the second conductive member is an INCONEL alloy. In some examples, the second conductive member is a copper-nickel foil. In some examples, the second conductive member is a cupronickel alloy. In some examples, the cupronickel alloy comprises 70% copper and 30% nickel. In some examples, the second conductive member is a CONSTANTAN alloy having 55% copper and 45% nickel.

The first conductive member and the second conductive member may be electrically coupled together using, e.g., one or more electrical joints. In some examples, the properties of the first conductive member and the second conductive member may be different. The electrical joints may be relatively difficult to form given the distinct properties of the different conductive members. Exemplary methods for forming a catheter include securing a first conductive member that includes a first material (e.g., copper) to a catheter body, securing a second conductive member that includes a second material (e.g., molybdenum), different from the first material, to the catheter body at a location distal of the first conductive member on the catheter body, and forming one or more electrical joints for electrically coupling and joining the first conductive member and the second conductive member. The electrical joints may be formed using tack welding, laser welding, crimping, wrapping stripped wires around each other, soldering, swagging, a conductive adhesive, ferrule pins, or a combination thereof. In some examples, the electrical joints are formed prior to positioning the first and second conductive members on the catheter body.

As used herein, the term "electrode" refers to an electrically conducting element (typically made of metal) that receives electrical current and subsequently releases the electrical current to another electrically conducting element. In the context of the present disclosure, electrodes are often positioned relative to each other, such as in an arrangement of an inner electrode and an outer electrode. Accordingly, as used herein, the term "electrode pair" refers to two electrodes that are positioned adjacent to each other such that application of a sufficiently high voltage to the electrode pair will cause an electrical current to transmit across the gap (also referred to as a "spark gap") between the two electrodes (e.g., from an inner electrode to an outer electrode, or vice versa; or from a proximal electrode to a distal electrode along the length of a catheter, or vice versa, optionally with the electricity passing through a conductive fluid or gas therebetween). In some contexts, one or more electrode pairs may also be referred to as an electrode assembly. In the context of the present disclosure, the term "emitter" broadly refers to the region of an electrode assembly where the current transmits across the electrode pair, generating a shock wave. The terms "emitter sheath" and "emitter band" refers to a continuous or discontinuous band of conductive material that may form one or more electrodes of one or more electrode pairs, thereby forming a location of one or more emitters. One or more of the emitters, emitter sheaths, emitter assemblies, and/or electrodes may be formed from a metal, such as stainless steel, copper, tungsten, platinum, palladium, molybdenum, cobalt, chromium, iridium, or an alloy or alloys thereof, such as cobalt-chromium, platinum-chromium, cobalt-chromium-platinum-palladium-iridium, or platinum-iridium, or a mixture of such materials.

In some embodiments, an IVL catheter is a so-called "rapid exchange-type" ("Rx") catheter provided with an opening portion through which a guide wire is guided (e.g., through a middle portion of a central tube in a longitudinal direction). In some embodiments, an IVL catheter may be an "over-the-wire-type" ("OTW") catheter in which a guide wire lumen is formed throughout the overall length of the catheter, and a guide wire is guided through the proximal end of a hub.

In the following description of the various embodiments, it is to be understood that the singular forms "a," "an," and "the" used in the following description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Certain aspects of the present disclosure include process steps and instructions described herein in the form of an algorithm. It should be noted that the process steps and instructions of the present disclosure could be embodied in software, firmware, or hardware and, when embodied in software, could be downloaded to reside on and be operated from different platforms used by a variety of operating systems. Unless specifically stated otherwise as apparent from the following discussion, it is appreciated that, throughout the description, discussions utilizing terms such as "processing," "computing," "calculating," "determining," "displaying," "generating" or the like, refer to the action and processes of a computer system, or similar electronic computing device, that manipulates and transforms data represented as physical (electronic) quantities within the computer system memories or registers or other such information storage, transmission, or display devices.

The present disclosure in some embodiments also relates to a device for performing the operations herein. This device may be specially constructed for the required purposes, or it may comprise a general-purpose computer selectively activated or reconfigured by a computer program stored in the computer. Such a computer program may be stored in a non-transitory, computer readable storage medium, such as, but not limited to, any type of disk, including floppy disks, USB flash drives, external hard drives, optical disks, CD-ROMs, magnetic-optical disks, read-only memories (ROMs), random access memories (RAMs), EPROMS, EEPROMs, magnetic or optical cards, application specific integrated circuits (ASICs), or any type of media suitable for storing electronic instructions, and each connected to a computer system bus. Furthermore, the computing systems referred to in the specification may include a single processor or may be architectures employing multiple processor designs, such as for performing different functions or for increased computing capability. Suitable processors include central processing units (CPUs), graphical processing units (GPUs), field programmable gate arrays (FPGAs), and ASICs.

The methods, devices, and systems described herein are not inherently related to any particular computer or other apparatus. Various general-purpose systems may also be used with programs in accordance with the teachings herein, or it may prove convenient to construct a more specialized apparatus to perform the required method steps. The structure for a variety of these systems will appear from the description below. In addition, the present invention is not described with reference to any particular programming language. It will be appreciated that a variety of programming languages may be used to implement the teachings of the present disclosure as described herein.

Although shock wave devices described herein generate shock waves based on high voltage applied to electrodes, it should be understood that a shock wave device additionally or alternatively may comprise a laser and optical fibers as a shock wave emitter system whereby the laser source delivers energy through an optical fiber and into a fluid to form shock waves and/or cavitation bubbles.

In the following description of the various embodiments, reference is made to the accompanying drawings, in which are shown, by way of illustration, specific embodiments that can be practiced. It is to be understood that other embodiments and examples can be practiced, and changes can be made without departing from the scope of the disclosure.

As provided herein, it should be appreciated that any disclosure of a numerical range describing dimensions or measurements such as thicknesses, length, weight, time, frequency, temperature, voltage, current, angle, etc. is inclusive of any numerical increment or gradient within the ranges set forth relative to the given dimension or measurement.

FIG. 1 illustrates an exemplary IVL catheter system according to one or more aspects of the disclosure. The catheter system includes a catheter 100, a conductive element such as an energy guide 172 for routing energy to the catheter 100, and a power source 170. The catheter 100 includes a catheter body 110 having a guide wire lumen for guiding the catheter 100 along a guide wire 160 to a treatment site. Catheter 100 also includes an enclosure 120 that surrounds at least a portion of the catheter body. The catheter 100 includes shock wave generating regions 101, 102, 103, 104, and 105 that are located along the catheter body 100. In response to delivery of energy from the power source 170, one or more shock waves are generated from one or more of the shock wave generating regions 101, 102, 103, 104, and 105. The catheter 100 may be configured such that one or more of the shock wave generating regions can generate shock waves independently of one or more of the remaining shock wave generating regions and/or may be configured such that all of the shock wave generating regions simultaneously generate shock waves. Although five shock wave generating regions are shown in FIG. 1, fewer shock wave generating regions (e.g., one, two, three, or four shock wave generating regions) may be included and/or more additional shock wave generating regions (e.g., six, seven, eight, nine, or ten shock wave generating regions) may be included, for instance, in shorter or in longer catheters for treating shorter or longer lesions.

Exemplary IVL catheter systems (such as the one shown in FIG. 1) are used for treating lesions in body lumens. In various examples, a lesion could be a calcified region of vasculature, a thrombus or an occlusion in vasculature, arteriosclerotic plaque, or a lesion in some other body lumen, such as a kidney stone in a ureter.

In one or more embodiments, each of the one or more of the shock wave generating regions 101, 102, 103, 104, and 105 includes an electrode assembly, which includes one or more electrode pairs. In some examples, the shock wave generating regions 101, 102, 103, 104, and 105 are formed from conductive metal sheaths and insulated wires positioned around or mounted onto an outer surface of the catheter body 110. In some examples, the shock wave generating regions 101, 102, 103, 104, and 105 are formed from exposed regions of a first and second wire positioned on the catheter body 110. High voltage pulses are supplied to the shock wave generating regions 101, 102, 103, 104, and 105 from a power source 170 external to the catheter 100. In some examples, the power source 170 includes a multiplexer for selectively applying a voltage across a particular shock wave generating region (e.g., 101) or a pair of shock wave generating region (e.g., 101 and 102), to generate shock waves at a desired position within the flexible polymer enclosure 102. Accordingly, shock wave generating regions or pairs of shock wave generating regions as shown can be connected on the same or separate electrical channels, with the flow of current to a given channel controlled via the multiplexer.

In some examples, at least one electrode pair is spaced a sufficient distance from at least one other electrode pair such that acoustic shock waves generated at the two electrode pairs do not constructively interfere with one another. In one or more examples, electrode pairs are spaced a relatively small distance apart from one another (e.g., one millimeter to four millimeters (1 mm-4 mm) apart) along the length of the catheter. Spacing the electrode pairs (e.g., of one of more shock wave generating regions 101, 102, 103, 104, and 105) a relatively small distance from one another promotes constructive interference between acoustic shock waves generated at the adjacent electrode pairs, thereby increasing the pressure of the combined shock wave. In one or more examples, the catheter can include one or more pairs of electrode pairs that are located at the same longitudinal location along the length of the catheter with the electrode pairs arranged circumferentially less than one hundred eighty degrees (180°) apart from each other. Arranging electrode pairs that are located at the same longitudinal location along the length of the catheter at an angle less than one hundred eighty degrees (180°) apart promotes constructive interference between acoustic shock waves generated at the adjacent electrode pairs, thereby increasing the pressure of the combined shock wave. In one or more examples, the catheter can include one or more pairs of electrode pairs that are located at the different longitudinal locations along the length of the catheter with the electrode pairs arranged circumferentially less than one hundred eighty degrees (180°) apart from each other.

In one or more examples, the gaps between the electrodes of a first and second electrode pair can be circumferentially aligned with one another relative to the catheter body 110 (e.g., the gap between the first electrode and second electrode of the first electrode pair can be located at the same location along the circumference of the catheter as the gap between the first electrode and second electrode of the second electrode pair) and separated by a distance (e.g., a longitudinal gap) between one millimeter (1 mm) and four millimeters (4 mm) along the length of the catheter such that the shock waves generated at the electrode pairs constructively interfere to produce a combined shock wave. In some examples, the gaps between the electrodes of each electrode pair can be circumferentially offset from one another relative to the catheter body 110 by an angle of less than one hundred eighty (180) degrees but located at essentially the same longitudinal location on the catheter body 110 such that the shock waves generated at the electrode pairs constructively interfere to produce a combined shock wave. In some examples, the first and second electrode pairs may be formed between an exposed portion of a first and second wire each separated by a spark gap from a conductive emitter band. In some examples, the first and second electrode pairs may each be formed by exposed portions of two wires separated by respective spark gaps.

Additional detail regarding exemplary options for electrode placement along the length of the catheter can be found in U.S. Pat. No. 11,779,363, which is incorporated herein by reference for all purposes, and in U.S. patent application Ser. No. 18/586,299, which is incorporated herein by reference for all purposes.

In one or more embodiments of the present disclosure, the power source 170 shown in FIG. 1 includes a high voltage pulse generator. In one or more embodiments, the power source 170 supplies a high voltage pulse no less than six kilovolts (6 kV). In one or more embodiments, the power source 170 supplies a high voltage pulse no less than ten kilovolts (10 kV). In one or more embodiments, the power source 170 supplies a high voltage pulse between three kilovolts (3 kV) and thirty kilovolts (30 kV). In one or more embodiments, the power source 170 supplies a high voltage pulse between six kilovolts (6 kV) and ten kilovolts (10 kV). In one or embodiments, the power source 170 is configured to supply a high voltage pulse that is adjustable in intensity. In some examples, the power source 170 applies an alternating current to the electrodes to induce a change in the polarity of the electrodes.

For treatment of an occlusion in a blood vessel, the voltage pulse applied by the power source 170 is typically in the range of from about five hundred to three thousand volts (500-3,000 V). In some implementations, the voltage pulse applied by the voltage source can be up to about ten thousand volts (10,000 V) or higher than ten thousand volts (10,000 V). The pulse width of the applied voltage pulses ranges is between two microseconds and six microseconds (2-6 μs). The repetition rate or frequency of the applied voltage pulses may be between about one hertz (1 Hz) and ten hertz (10 Hz). The total number of pulses applied by the power source 170 may be, for example, sixty (60) pulses, eighty (80) pulses, one hundred twenty (120) pulses, three hundred (300) pulses, up to five hundred (500) pulses, or other increments of pulses within this range. Alternatively, or additionally, in some examples, the power source 170 may be configured to deliver a packet of micro-pulses having a sub-frequency between about one hundred hertz to ten kilohertz (100 Hz to 10 kHz). The preferred voltage, repetition rate, and number of pulses may vary depending on, e.g., the size of the lesion, the extent of calcification, the size of the blood vessel, the attributes of the patient, or the stage of treatment. For instance, a physician may start with low energy shock waves and increase the energy as needed during the procedure, or vice versa. The magnitude of the shock waves can be controlled by controlling the voltage, current, duration, and repetition rate of the pulsed voltage from the power source 170. Additional detail regarding voltage pulsing, repetition rate, number of pulses, etc., can be found in U.S. patent application Ser. No. 18/595,148, which is incorporated herein by reference in its entirety for all purposes.

The application of a relatively high voltage pulse (e.g., greater than or equal to ten kilovolts (10 kV)) may be beneficial for treating certain types of lesions (e.g., lesions associated with aortic valve stenosis) that necessitate a higher sonic output for treatment. In some examples, the high voltage pulses are applied at a voltage of at least at least one kilovolt (1 kV), at least two kilovolts (2 kV), at least three kilovolts (3 kV), at least four kilovolts (4 kV), at least five kilovolts (5 kV), at least six kilovolts (6 kV), at least seven kilovolts (7 kV), at least eight kilovolts (8 kV), at least nine kilovolts (9 kV), at least ten kilovolts (10 kV), at least eleven kilovolts (11 kV), at least twelve kilovolts (12 kV), at least thirteen kilovolts (13 kV), at least fourteen kilovolts (14 kV), at least fifteen kilovolts (15 kV), at least sixteen kilovolts (16 kV), at least seventeen kilovolts (17 kV), at least eighteen kilovolts (18 kV), at least nineteen kilovolts (19 kV), at least twenty kilovolts (20 kV), and/or at least thirty kilovolts (30 kV). The high voltage pulses may be no more than thirty kilovolts (30 kV), no more than twenty kilovolts (20 kV), no more than nineteen kilovolts (19 kV), no more than eighteen kilovolts (18 kV), no more than seventeen kilovolts (17 kV), no more than sixteen kilovolts (16 kV), no more than fifteen (15 kV), no more than fourteen kilovolts (14 kV), no more than thirteen kilovolts (13 kV), no more than twelve kilovolts (12 kV), no more than eleven kilovolts (11 kV), no more than ten kilovolts (10 kV), no more than nine kilovolts (9 kV), no more than eight kilovolts (8 kV), no more than seven kilovolts (7 kV), no more than six kilovolts (6 kV), no more than five kilovolts (5 kV), no more than four kilovolts (4 kV), no more than three kilovolts (3 kV), no more than two kilovolts (2 kV), and/or no more than one kilovolts (1 kV).

The voltage pulses may be applied at a rate of a rate of between one hertz (1 Hz) and fifty hertz (50 Hz), including one hertz (1 Hz) and fifty hertz (50 Hz). The power source 170 may be configured to deliver the voltage pulses at a rate of a rate of up to one hundred hertz (100 Hz), up to ninety hertz (90 Hz), up to eighty hertz (80 Hz), up to seventy hertz (70 Hz), up to sixty hertz (60 Hz), up to fifty hertz (50 Hz), up to forty hertz (40 Hz), up to thirty hertz (30 Hz), up to twenty hertz (20 Hz), and/or up to ten hertz (10 Hz). The power source 170 may be configured to deliver the voltage pulses at a rate of at least ten hertz (10 Hz), at least twenty hertz (20 Hz), at least thirty hertz (30 Hz), at least forty hertz (40 Hz), at least fifty hertz (50 Hz), at least sixty hertz (60 Hz), at least seventy hertz (70 Hz), at least eighty hertz (80 Hz), at least ninety hertz (90 Hz), at least one hundred hertz (100 Hz), and/or at least two hundred hertz (200 Hz).

The enclosure 120 shown in FIG. 1, in one or more embodiments, is a balloon (e.g., an angioplasty balloon). The enclosure 120 may be in a collapsed or deflated configuration to provide a lower profile during delivery to the treatment site. During treatment, the enclosure 120 may be inflated to a low pressure (e.g., less than ten atmospheres (10 atm) or between two and four atmospheres (2-4 atm)) with a liquid fluid (e.g., saline, contrast, or a mixture). Energy is then provided to shock wave generating regions 101, 102, 103, 104, and 105 resulting in the generation of one or more shock waves. The enclosure may then be deflated and reinflated to flush out any accumulated gas bubbles before further treatment at that site. The enclosure 120 may alternatively be advanced further to a different lesion (or different section of the same lesion) or withdrawn from the patient.

In some examples, one or more sensors 107 are positioned along the catheter 100. The sensors 107 may be positioned at any location on catheter 100. For instance, the sensors 107 may be positioned proximal to one or more shock wave generating regions 101, 102, 103, 104, and/or 105, distal from one or more shock wave generating regions 101, 102, 103, 104, and/or 105, and/or intermediary between one or more shock wave generating regions 101, 102, 103, 104, and/or 105 (or any combination thereof). The sensors 107 may be positioned external to the enclosure 120 and/or outside of a patient. For instance, certain sensors, such as a pressure sensor, may be positioned outside of the enclosure 120 and/or the patient because the pressure may be measured on the system as a whole when components are in fluid communication. The sensors may include one or more of any suitable sensor devices, such as a pressure sensor, a thermal sensor, an electrical sensor (e.g., current, voltage, resistance, and/or impedance sensors), or a visualization element. Sensors 107 can provide feedback to an operator using catheter 100 by measuring parameters in the surrounding environment and thereby indicating a status of the catheter 100 and components thereof, and further providing for guidance on what further steps the operator may decide to implement with catheter 100. For example, in implementations where sensor devices 107 include pressure sensors, a slight decrease in pressure may indicate success at cracking a calcified lesion, due to the fact that the expandable member surrounding the emitters is able to further expand without changing the volume of fluid within the expandable member. Further, a significant decrease in pressure may indicate a rupture failure mode where the expandable member has lost seal and fluid volume, and thus guiding toward withdrawal of the device. In implementations where the sensor devices include a visualization element, an operator of the catheter 100 may be able to more clearly understand where the catheter device 100 is located relative to a target lesion or anatomy, prior to, during, and after delivering therapy.

In some embodiments, the application of high voltage pulses and/or application of a large number of pulses over time to shock wave generating regions 101, 102, 103, 104, and 105 can result in degradation of the electrodes. Degradation of the electrodes may, over time, result in less reliable shock wave generation and/or reduced sonic output. Further deterioration of the electrodes can result in shrapnel during shock wave generation, which can puncture enclosures (e.g., angioplasty balloons) surrounding the electrodes and/or lead to device failure.

Forming the electrodes from a material that is relatively more resistant to wear can improve electrode durability, thus enhancing the longevity of shock wave generating catheters. Such materials having a higher durability may present one or more challenges. For instance, such materials may provide significantly lower conductivity (which may impede performance of the power source 170) and may result in a catheter having reduced navigability due to higher stiffness/hardness of the material (e.g., if used for wiring along the length of a relatively significant portion of the catheter). The challenges presented by these relatively more durable materials, however, may be overcome by using a first material having a relatively lower stiffness and relatively higher conductivity to conduct electrical energy from the power source along the length of the catheter 100, and using a second, relatively more durable, material with a relatively higher stiffness and lower conductivity near the distal end of the catheter to conduct electricity to the one or more shock wave generating regions 101, 102, 103, 104, and 105. In some examples, at least one of the electrodes of at least one shock wave emitter of shock wave generating regions 101, 102, 103, 104, and 105 may be formed of the relatively more durable material, which may result in a shock wave emitter having greater longevity and reliability (relative of emitters with electrodes formed of the first material) for the reasons described above. An example of a catheter including two conductive members formed of different materials is described below with reference to FIG. 2.

Figure 2:
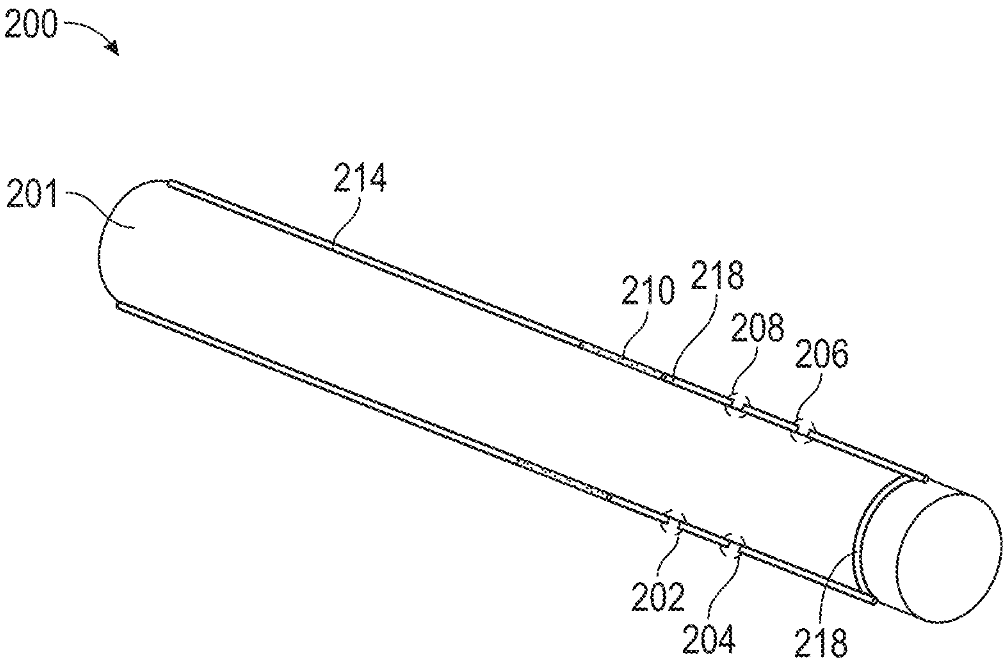
FIG. 2 illustrates an exemplary catheter including an electrical joint that electrically couples conductive members, according to some examples.

FIG. 2 illustrates a catheter 200 that may be used for catheter 100 of FIG. 1. Catheter 200 includes a catheter body 201 and a plurality of shock wave emitters 202, 204, 206, and 208 positioned along the catheter body 201. At least two different conductive members 214 and 218 may be positioned on catheter body 201 to conduct electricity to at least one of the shock wave emitters 202, 204, 206, and 208. Conductive member 214 may include a first conductive wire electrically coupled to a power source (e.g., power source 170) and may conduct electricity from the power source to conductive member 218. Conductive member 218 may include a second conductive wire electrically coupled to conductive member 214 and configured to conduct electricity from conductive member 214 to at least one of the shock wave emitters 202, 204, 206, and 208. One or more of the shock wave emitters 202, 204, 206, and 208 include a pair of electrodes separated by a spark gap. In some embodiments, at least one of the electrodes of the one or more shock wave emitters may be formed from conductive member 218. In the example depicted in FIG. 2, conductive member 218 is an insulated wire and the electrodes of each of shock wave emitters 202, 204, 206, and 208 are formed by an exposed end of conductive member 218. The electrodes are separated by spark gaps that may be formed by cutting conductive member 218 and spacing the exposed conductive wire apart by respective spark gaps.

The at least two conductive members 214 and 218 may be respectively formed from at least two different (e.g., distinct) materials. That is, conductive member 214 may include a first material, and conductive member 218 may include a second material different from the first material. The first material and the second material may have different properties (e.g., different electrical and/or mechanical properties). For example, the second material of conductive member 218 may include at least one of: a lower conductivity, a higher stiffness, a higher density, a higher melting point, and a higher resistivity relative to the first material. In some examples, the first material of conductive member 214 may include at least one of: a higher conductivity, a lower stiffness, a lower density, a lower melting point, and a lower resistivity relative to the second material. In some examples, the first material may comprise copper, aluminum, gold, etc., and the second material may comprise molybdenum, tungsten, rhodium, rhenium, tantalum, niobium, or a combination thereof, such as an alloy or a clad wire. In some examples, the first and second material are insulated using a polyimide insulation material. In some examples, the thickness of the insulation for the first and second materials is the same. In some examples, a different thickness of the insulation material is used for the first material than the second material.

Conductive member 214 may be positioned at least partially proximally of conductive member 218 on the catheter body 201 and may be disposed along the majority of the length of the catheter body 201 of catheter 200. The second conductive member 218 may be positioned at or near the distal end of the catheter body 201 (e.g., at least partially distally of conductive member 214). In some examples, conductive member 218 may be positioned such that it is located entirely distally of conductive member 214. In some examples, one or more portions of conductive member 214 and conductive member 218 may overlap with one another. Such overlapping portions may form at least a portion of one or more electrical joints, as described below. For instance, at least a portion of the first and second conductive member may be positioned to overlap with one another and welded together (e.g., using resistance welding or laser welding). This relative configuration of the first and second conductive members 214 and 218 may provide several technical advantages given the respective material properties of conductive members 214 and 218 described above. For example, by utilizing conductive member 214 along the majority of the length of the catheter 200, the stiffness and resistivity of the wiring for the overall catheter 200 may be relatively low (compared to, e.g., a design that may utilize the molybdenum, tungsten, rhodium, rhenium, tantalum, niobium, clad wire along the entire length of the catheter). The lower overall stiffness and resistivity may be due to utilizing more (e.g., higher percentage such as 60%, 70%, 80%, etc.) of the first material (e.g., copper), having lower stiffness and higher conductivity, than the second material (e.g., molybdenum), having higher stiffness and lower conductivity.

In some examples, between five millimeter (5 mm) and fifteen millimeter (15 mm) of the second material are utilized along the length of the catheter, and between one hundred twenty-five centimeters (125 cm) and three hundred centimeters (300 cm) of the first material are utilized along the length of the catheter. In some examples, the first material is utilized along 90% or more of the length of the catheter, and the second material is utilized along less than 10% of the length of the catheter. In some examples, the first material is utilized along more than 95% or more of the length of the catheter, and the second material is utilized along less than 5% of the length of the catheter. In some examples, the first material is utilized along more than 97% or more of the length of the catheter, and the second material is utilized along less than 3% of the length of the catheter. In some examples, the first material is utilized along 98% or more of the length of the catheter, and the second material is utilized along less than 2% of the length of the catheter.

In examples where there is the catheter comprises less of conductive member 218 (and thus less of the second material) relative to conductive member 214, any detrimental effects resulting from second conductive member 218's relatively high resistivity and stiffness to shock wave generation and/or catheter deliverability may be reduced (including minimized). Moreover, as noted, the second material may be used as at least a portion (e.g., one or more electrodes) of one or more of the shock wave emitters 202, 204, 206, and/or 208. Thus, the electrodes of those shock wave emitters may have increased longevity given the relatively higher durability (e.g., ability to withstand repeated stresses of shock wave generation) of the second material (e.g., molybdenum) of conductive member 218, that reduces the pace at which the emitters erode relative to a design in which the first material (e.g., copper) is used for the emitter electrodes. By slowing the emitter degradation, the catheter 200 may be used for a greater number of cycles, and thus be used in the treatment of more patients.

The dissimilarities between the first conductive member 214 and the second conductive member 218, however, makes electrically coupling the two conductive members challenging. Techniques for forming electrical joints 210 between conductive member 214 and the conductive member 218 having such dissimilar properties are described herein. The electrical joints 210 may be formed according to a number of different process, including, but not limited to, resistance welding, soldering, laser welding, mechanical fastening, and/or conductive adhesion. The electrical joints 210 may be located at any position along the length of the catheter body. In some examples, the electrical joints 210 are positioned within enclosure 120. In some examples, the electrical joints 210 are positioned proximally of and exterior to the enclosure 120. In some examples, the electrical joints are positioned between zero to ten centimeters (0-10 cm) proximally of a proximal end of the enclosure. In some examples, the electrical joints are positioned between zero to five centimeters (0-5 cm) proximally of a proximal end of the enclosure. In some examples, the electrical joints are positioned between one to two centimeters (1-2 cm) proximally of a proximal end of the enclosure. In some examples, the electrical joints are positioned between zero to ten millimeters (0-10 mm) proximally of a proximal end of the enclosure. In some examples, positioning the electrical joints proximally of the enclosure may be desirable because pleating and folding the enclosure may not be impacted by nor impact the electrical joint. The electrical joints 210 may be embedded in catheter body 110. The electrical joints 210 may be embedded such that an outer diameter of the electrical joint 210 is flush with an outer diameter of the catheter body 210. An overview of various electrical joint configurations is provided below, and additional detail related to the formation of such joints is provided with reference to FIG. 3.

Example Connectors

In some examples, the one or more electrical joints 210 that electrically couple the conductive member 214 to conductive member 218 include an electrical connector. The connector may be a conductive cylinder or terminal pin (e.g., ferrule pin) including copper, brass, silver, tin, stainless steel, etc., or a combination thereof. The one or more electrical joints 210 may include a conductive cylinder, a crimp-on connector, a twist-on connector, a push-in wire connector, a terminal pin (e.g., ferrule pin) or any other type of wire connector capable of electrically coupling the first conductive member 214 and second conductive member 218. The connector may include copper, brass, silver, tin, stainless steel, etc., or a combination thereof. The connector may be coated or plated with at least one of nickel plating, chromium plating, nickel coating, chromium coating, or a combination thereof.

Example Conductive Adhesives

In some examples, the one or more electrical joints 210 that electrically couple the conductive member 214 to conductive member 218 include a conductive adhesive. The conductive adhesive may include at least one of silver, carbon graphite, gold, diamond, copper, and aluminum, platinum, nickel, and carbon. The conductive adhesives used for the electrical joints described herein may have a relatively strong mechanical bond strength (e.g., tensile strength), and relatively high conductivity/low resistance. The tensile strength of the conductive adhesive is dependent on the area. In some examples, the tensile strength of the conductive adhesive may be between one Newton (1 N) and twenty-five Newtons (25 N). For instance, with nine thousandths of an inch (0.009 in) and eleven thousandths of an inch (0.011 in) conductive members, the tensile strength ranged from ten Newtons to fifteen Newtons (10 N-15 N). The resistance is also dependent on the length and materials of the conductive members. In some examples, the maximum resistance is one ohm (1Ω). In some examples, however, the resistance may exceed one ohm (1Ω). The conductive adhesives that may be utilized for the joints described herein include a sufficient density of conductive material to prevent arching at high voltages, a stable shelf life (e.g., are non-corrosive), and may operate with a sufficient hardening of adhesive to prevent movement/migration of conductive material.

Example Soldered Joints

In some examples, the one or more electrical joints 210 that electrically couple the conductive member 214 to conductive member 218 include a soldered joint. In some examples, forming a soldered joint includes overlapping the conductive member 214 with conductive member 218 by between one millimeter (1 mm) and five millimeters (5 mm) (e.g., one millimeter (1 mm), two millimeters (2 mm), three millimeters (3 mm)) and soldering a joint. In some examples the joint may additionally or alternatively be formed by swaging. In examples where the joint is a soldered joint, at least a portion of the second conductive member 218 may be coated or plated with a coating or plating that facilitates a soldered connection with the first conductive member 214. In some examples, the coating or plating may include the first material (e.g., copper). The coating or plating may include a nickel-copper coating or plating which may include between zero to ten microns (0-10 μm) of nickel and between one hundred to two hundred (e.g., 150) microns (100-200 μm) of copper. In some examples, the coating or plating may include between 0% and 5% nickel and between 100% and 95% copper. In some examples, the coating or plating may include between 0% and 10% nickel and between 100% and 90% copper. In some examples, the ratio of copper to nickel of the plating may be between 200 to 1 and 10 to 1. In some examples, the coating or plating may be a nickel-chromium plating (e.g., 50% nickel, 50% chromium). In some examples, the coating or plating may include any non-toxic element that can solder to copper. The coating or plating may provide a relatively stronger soldered joint than a soldered joint with no coating or plating. Additionally, or alternatively, at least a portion of the first conductive member may be coated or plated with a coating or plating that facilitates a soldered connection with the second conductive member 218 (e.g., a coating or plating including the second material). While described with reference to soldered joints, it should be understood that the coating and/or plating may be applied to at least a portion of either or both of conductive members 214 and 218 in any of the embodiments described herein (e.g., for rust prevention).

Example Welded Joints

In some examples, the one or more electrical joints 210 may include a welded joint. Different types of welds may be utilized in forming the one or more electrical joints 210. For instance, one or more of the electrical joints 210 may formed by laser welding, resistance welding, tack welding, or otherwise welding the first conductive member 214 to the second conductive member 218. An electrical joint 210 formed by welding may be desirable for its relatively smooth transition (e.g., compared to a soldered joint or connector) between conductive member 214 and conductive member 218.

Figure 3:
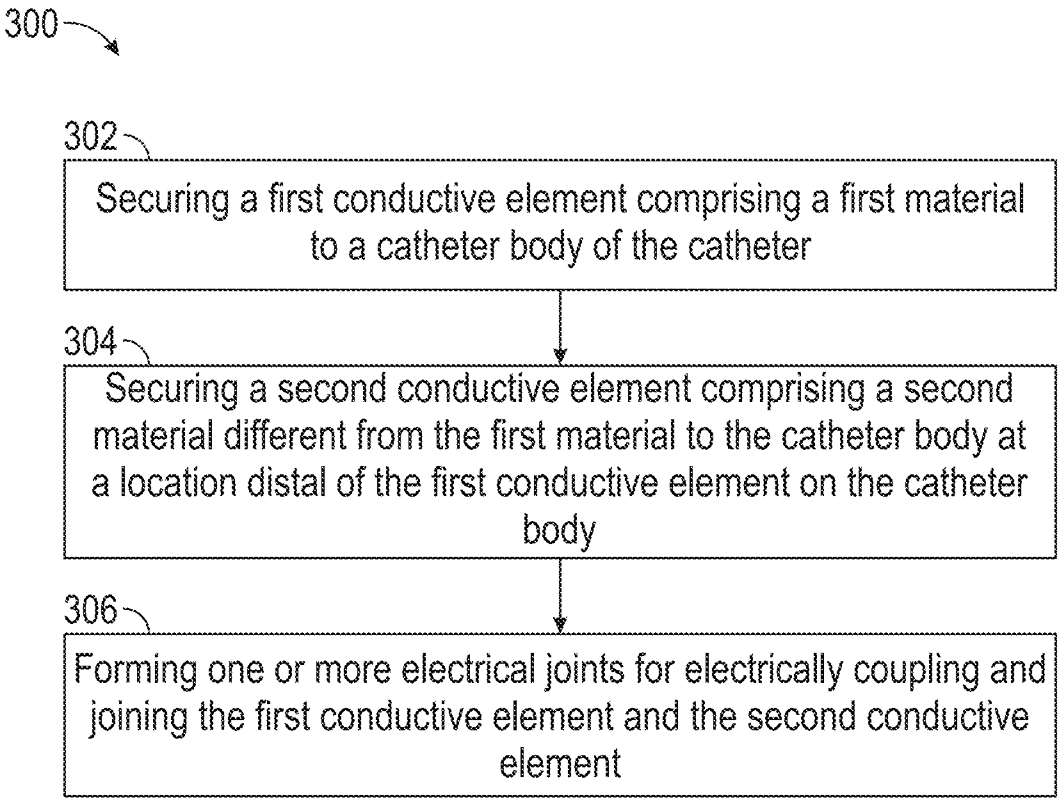
FIG. 3 illustrates an exemplary method for forming a catheter including electrical joints configured to electrically couple a first conductive member to a second conductive member, according to some examples.

A variety of different methods may be utilized to form the catheters (e.g., catheter 100 and/or 200) including the electrical joints described above with reference to FIG. 2. FIG. 3 illustrates an exemplary method 300 for forming a catheter that includes one or more electrical joints configured to electrically couple a first conductive member of the catheter to a second conductive member of the catheter.

At block 302, the method includes securing a first conductive member (e.g., conductive member 214) that includes a first material to a catheter body. In some examples, securing the first conductive member to the catheter body may include positioning the first conductive member within a groove (e.g., cavity) along an outer surface of the catheter body. In some examples, the first conductive member may be secured to the catheter body using, e.g., a top coat material. The top coat material may be an adhesive that secures the conductive member to a surface (e.g., a groove/cavity) of the catheter body. In some examples, the first material of the first conductive member includes any of the properties described above with the first material included in conductive member 214 of FIG. 2. For instance, the first material may include at least one of: a lower stiffness, a lower density, a lower melting point, a lower resistivity, and a higher conductivity relative to the second material. In some examples, the first material may be copper.

At block 304, the method includes securing a second conductive member (e.g., conductive member 218) comprising a second material different from the first material to the catheter body at a location distal of the first conductive member on the catheter body. Conductive member 218 may similarly be secured in a groove/cavity along the outer surface of the catheter body. In some examples, the second conductive member may be secured to the catheter body using, e.g., a top coat material. The top coat material may be an adhesive that secures the conductive member to a surface (e.g., a groove/cavity) of the catheter body. In some examples, the second material of the second conductive member includes any of the properties described above with reference to the second material included in conductive member 218 of FIG. 2. For instance, the second material may include at least one of: a higher stiffness, a higher density, a higher melting point, and a higher resistivity relative to the first material.

At block 306, the method includes forming one or more electrical joints for electrically coupling and joining the first conductive member and the second conductive member. As described above with reference to FIG. 2, a variety of electrical joints (e.g., welded joints, soldered joints) may be implemented according to the examples disclosed herein. Different types of electrical joints may be formed according to different steps than others. In some examples, the joints may be formed prior to securing the conductive members to the catheter body.

In some examples, forming the one or more electrical joints includes inserting the first conductive member into a connector, inserting the second conductive member into the connector, and crimping the connector to the first conductive member and the second conductive member. The connector may include a crimp-on connector, a twist-on connector, a push-in wire connector, a terminal pin (e.g., ferrule pin) or any other type of wire connector capable of electrically coupling the first conductive member 214 and second conductive member 218. The connector may include copper, brass, silver, tin, stainless steel, etc., or a combination thereof. The connector may be coated or plated with at least one of nickel plating, chromium plating, nickel coating, chromium coating, or a combination thereof.

In some examples, forming the one or more electrical joints includes applying pressure to the first conductive member and the second conductive member, passing current through the first conductive member, the second conductive member, or both to generate heat, and melting at least one of the first conductive member and the second conductive member to join the two members together. In some examples, forming the one or more electrical joints includes flattening at least a portion of the first conductive member and/or the second conductive member. In some examples, forming the one or more electrical joints includes flowing an inert gas over at least a portion of the first conductive member and the second conductive member. For instance, in examples where the electrical joint(s) are formed using resistance welding, flowing an inert gas over at least a portion of the first conductive member and the second conductive member during the welding process may reduce or prevent undesirable chemical reactions (e.g., oxidation, hydrolysis) that could degrade the quality of the weld. In some examples, the inert gas is nitrogen, argon, or other inert gas. The first and second conductive member may be uncoated in examples where the electrical joint is formed via resistance welding.

In some examples, when the electrical joint(s) are formed using resistance welding, one or both of the first and second conductive member have a diameter (e.g., wire gauge) of between three thousandths of an inch (0.003 in) and one hundredth of an inch (0.010 in). In some examples, the first conductive member and the second conductive member have the same diameter (e.g., wire gauge). In some examples, one or both of the first and second conductive member have a diameter of at least three thousandths of an inch (0.003 in), of at least four thousandths of an inch (0.004 in), of at least five thousandths of an inch (0.005 in), of at least six thousandths of an inch (0.006 in), of at least seven thousandths of an inch (0.007 in), of at least eight thousandths of an inch (0.008 in), of at least nine thousandths of an inch (0.009 in), and/or of at least one hundredth of an inch (0.010 in). In some examples, one or both of the first and second conductive member have a diameter of at most three thousandths of an inch (0.003 in), of at most four thousandths of an inch (0.004 in), of at most five thousandths of an inch (0.005 in), of at most six thousandths of an inch (0.006 in), of at most seven thousandths of an inch (0.007 in), of at most eight thousandths of an inch (0.008 in), of at most nine thousandths of an inch (0.009 in), and/or of at most one hundredth of an inch (0.010 in).

In some examples, when the electrical joint(s) are formed using resistance welding, a pressure/force may be applied to the first and second conductive member, as noted above. The force applied during resistance welding may be between one Newton (1 N) and five Newtons (5 N). In some examples, the force applied during resistance welding may be at least one Newton (1 N), at least two Newtons (2 N), at least three Newtons (3 N), at least four Newtons (4 N), or at least five Newtons (5 N). In some examples, the force applied during resistance welding may be at most one Newton (1 N), at least most Newtons (2 N), at most three Newtons (3 N), at least most Newtons (4 N), or at most five Newtons (5 N).

In some examples, when the electrical joint(s) are formed using resistance welding, after applying a pressure to the first conductive member and the second conductive member, a current may be applied to the first and second conductive members. The current may be between one amperes (1 A) and five amperes (5 A). The current may be between one amperes (1 A) and three amperes (3 A). In some examples, the current applied may be at least one amperes (1 A), at least two amperes (2 A), at least three amperes (3 A), at least four amperes (4 A), and/or at least five amperes (5 A). In some examples, the current applied may be at most one amperes (1 A), at most two amperes (2 A), at most three amperes (3 A), at most four amperes (4 A), and/or at most five amperes (5 A). In some examples, a corresponding voltage applied across the first and second conductive members during resistance welding may be between one volt (1V) and three volts (3V). In some examples, the voltage applied may be at least five tenths of a volt (0.5V), at least one volt (1V), at least two volts (2V), at least three volts (3V), at least four volts (4V), and/or at least five volts (5V). In some examples, the voltage applied may be at most five tenths of a volt (0.5V), at most one volt (1V), at most two volts (2V), at most three volts (3V), at most four volts (4V), and/or at most five volts (5V).

In some examples, when the electrical joint(s) are formed using resistance welding, the current may be applied for between one tenths of a second (0.1 sec) and three seconds (3.0 secs) per resistance weld. In some examples, the current may be applied for between twenty-five hundredths of a second (0.25 sec) and two seconds (2.0 secs) per resistance weld. In some examples, the current may be applied for at least twenty-five hundredths of a second (0.25 sec), at least five tenths of a second (0.50 sec), at least seventy-five thousands of a second (0.75 sec), at least one second (1.0 sec), at least one and twenty-five hundredths of a second (1.25 secs), at least one and five tenths of a second (1.5 secs), at least one and seventy-five thousands of a second (1.75 secs), at least two seconds (2.0 secs), at least two and twenty-five hundredths of a second (2.25 secs), at least two and five tenths of a second (2.5 secs), at least two and seventy-five thousands of a second (2.75 secs), and/or at least three seconds (3.0 secs). In some examples, the current may be applied for at most twenty-five hundredths of a second (0.25 sec), at most five tenths of a second (0.50 sec), at most seventy-five thousands of a second (0.75 sec), at most one second (1.0 sec), at most one and twenty-five hundredths of a second (1.25 secs), at most one and five tenths of a second (1.5 secs), at most one and seventy-five thousands of a second (1.75 secs), at most two seconds (2.0 secs), at most two and twenty-five hundredths of a second (2.25 secs), at most two and five tenths of a second (2.5 secs), at most two and seventy-five thousands of a second (2.75 secs), and/or at most three seconds (3.0 secs).

In some examples, when the electrical joint(s) are formed using resistance welding, an inert gas may be supplied for between zero and ten seconds (0-10 secs) (s). In some examples, the inert gas may be supplied for at least one second (1 sec), at least two seconds (2 secs), at least three seconds (3 secs), at least four seconds (4 secs), at least five seconds (5 secs), at least six seconds (6 secs), at least seven seconds (7 secs), at least eight seconds (8 secs), at least nine seconds (9 secs), or at least ten seconds (10 secs). In some examples, the inert gas may be supplied for at most one second (1 sec), at most two seconds (2 secs), at most three seconds (3 secs), at most four seconds (4 secs), at most five seconds (5 secs), at most six seconds (6 secs), at most seven seconds (7 secs), at most eight seconds (8 secs), at most nine seconds (9 secs), or at most ten seconds (10 secs).

In some examples, the first conductive member may have a melting temperature of within two thousand five hundred degrees Celsius (2,500° C.) of the melting temperature of the second conductive member. In some examples, the first conductive member may have a melting temperature of within two thousand degrees Celsius (2,000° C.) of the melting temperature of the second conductive member. In some examples, the first conductive member may have a melting temperature of within one thousand seven hundred fifty degrees Celsius (1,750° C.) of the melting temperature of the second conductive member. In some examples, the first conductive member may have a melting temperature of within one thousand six hundred fifty degrees Celsius (1,650° C.) of the melting temperature of the second conductive member. In some examples, the first conductive member may have a melting temperature of within one thousand five hundred fifty degrees Celsius (1,550° C.) of the melting temperature of the second conductive member. In some examples, the first conductive member may have a melting temperature of within one thousand five hundred forty degrees Celsius (1,540° C.) of the melting temperature of the second conductive member.

It should be understood that any combination of the above parameters may be applicable to the resistance welding process. In some examples, resistance welds may be formed by applying a relatively higher current and/or voltage for a relatively shorter time and/or by applying a relatively lower current and/or voltage for a relatively longer time. In some examples, resistance welds may be formed by applying a current for a relatively longer time at a relatively lower pressure and/or a by applying a current for a relatively shorter time at a relatively higher pressure. In some examples, current and/or pressure may be varied (e.g., increased or decreased) to maintain a desired operational temperature during resistance welding. Below is a table of both the exemplary parameters that may be utilized to form electrical joints using resistance welding (e.g., copper and molybdenum).

TABLE 1

| Member 1 Size (inches) | Member 2 Size (inches) | Current (amperes) | Time (seconds) | Pressure (Newtons) | Gas (seconds) |
|---|---|---|---|---|---|
| .006 in | .005 in | 1.2 A | 2.0 s | 4.5 N | 7 s |
| .005 in | .003 in | 2.3 A | 0.6 s | 1.7 N | 3 s |
| .007 in | .004 in | 1.7 A | 1.2 s | 2.8 N | 5 s |
| .008 in | .006 in | 1.9 A | 1.1 s | 3.4 N | 4 s |

In some examples, forming one or more electrical joints includes clamping the first conductive member and the second conductive member and heating the first conductive member and the second conductive member to melt at least one of the conductive members to join the members together. Heating the first conductive member and the second conductive member to melt at least one of the conductive members to join the members together may include using a laser (e.g., to laser weld the two members together). In some examples, forming one or more electrical joints by laser welding includes clamping a higher-melting point conductive member to a mounting member and aligning the higher-melting point conductive member with the laser (e.g., to a crosshair of the laser). In some examples, aligning the higher-melting conductive member includes aligning an end of the higher-melting point conductive member with the laser (e.g., with the crosshair). In some examples, forming one or more electrical joints by laser welding includes calibrating the laser welder to the focused height. In some examples, forming one or more electrical joints by laser welding includes clamping another lower-melting point conductive member to a mounting member and positioning it adjacent to the higher-melting point conductive member aligned with the laser crosshairs. In some examples, the two conductive members are positioned such that their respective ends are in contact. In some examples, after positioning the two conductive members adjacent to one another, the laser is pulsed to heat the higher-melting point conductive member aligned with the crosshairs. After heating the higher-melting point conductive member aligned with the crosshairs, the laser crosshairs may be aligned with the other lower-melting point conductive member. The laser may again be pulsed to melt the lower-melting point conductive member. The lower-melting point conductive member may be pushed into the higher-melting point conductive member as it melts to form the electrical joint.

In some examples, the lower-melting point conductive member may be pushed into the higher-melting point conductive member such that the two members overlap between one tenths of a millimeter (0.1 mm) and two and five tenths of a millimeter (2.5 mm) to form the electrical joint. In some examples, pushing the lower-melting point conductive member into the higher-melting point conductive member causes the lower-melting point conductive member to form a bead on the higher-melting point conductive member. The bead may have an outer diameter less than or equal to an insulation layer disposed on a portion of each of the two conductive members. In some examples, the laser may be pulsed between 0-5 (e.g., 0, 1, 2, 3, 4, 5) times on the higher melting point conductive member and between 1-10 (e.g., 1, 2, 3, 4, 5, 6, 7, 8, 9, 10) times on the lower melting point conductive member. In some examples the higher-melting point conductive member is molybdenum, and the lower-melting point conductive member is copper.

In some examples, forming the one or more electrical joints by laser welding includes positioning an insulative layer around electrical joint. In some examples, the insulative layer includes a polyamide tube and/or an insulative coating. In some examples, the polyamide tube is adhered to the conductive members with adhesive. In some examples, the joined conductive members and insulative layer are embedded in the catheter body (e.g., in a groove of the catheter body). In some examples, embedding the conductive members and insulative layer includes heading the conductive members and insulative layer to secure the conductive members and insulative layer to the catheter body.

Forming the one or more electrical joints using laser welding may maintain a smaller cross-sectional profile of the catheter relative to soldering. For instance, soldering requires the addition of material to form an electrical joint. This may produce in an electrical joint having a relatively larger cross-sectional area (e.g., diameter) than a laser welded joint. Such a larger cross-sectional area may require deeper grooves in the catheter to maintain the same overall catheter profile, or without such deeper grooves, may increase the overall catheter profile. Using laser welding, no additional material is required. Moreover, the two conductive members being joined do not need to be overlapped with one another. Thus, forming the electrical joints using laser welding may result in a relatively more navigable device, with a relatively smaller profile, compared to a device using soldered joints. Further, because laser welded joints do not require additional materials (e.g., solder), laser welded joints may be relatively more biocompatible compared to soldered joints.

A variety of laser welders and welding parameters may be used to form the electrical joints described herein. In some examples, a Nd:YAG one thousand sixty-four nanometer (1,064 nm) laser may be used to form the one or more electrical joints. In some examples, other laser systems may be used, such as solid-state lasers or gas lasers (e.g., a $CO_2$ laser with ten and six tenths of a micrometer (10.6 μm) wavelength or another mid-infrared wavelength).

In some examples where a joint is formed by laser welding the two members together, the laser welder may have a peak power of between one tenth to ten kilowatts (0.1-10 kW). In some examples, the laser welder may have a peak power of at least one tenth of a kilowatt (0.1 kW), at least five tenths of a kilowatt (0.5 kW), at least one kilowatt (1 kW), at least two kilowatts (2 kW), at least three kilowatts (3 kW), at least four kilowatts (4 kW), at least five kilowatts (5 KW), at least six kilowatts (6 kW), at least seven kilowatts (7 kW), at least eight kilowatts (8 kW), at least nine kilowatts (9 kW), or at least ten kilowatts (10 KW). In some examples, the laser welder may have a peak power of at most ten kilowatts (10 KW), at most nine kilowatts (9 kW), at most eight kilowatts (8 kW), at most seven kilowatts (7 kW), at most six kilowatts (6 kW), at most five kilowatts (5 kW), at most four kilowatts (4 kW), at most three kilowatts (3 kW), at most two kilowatts (2 kW), at most one kilowatt (1 kW), at most five tenths of a kilowatt (0.5 kW), or at most one tenth of a kilowatts (0.1 kW).

In some examples where a joint is formed by laser welding the two members together, the weld time (e.g., weld length) may be between five tenths to fifteen milliseconds (0.5-15 ms). In some examples the weld time (e.g., weld length) may be at least five tenths of a millisecond (0.5 ms), at least seventy-five hundredths of a millisecond (0.75 ms), at least one millisecond (1 ms), at least two milliseconds (2 ms), at least three milliseconds (3 ms), at least three milliseconds (3 ms), at least four milliseconds (4 ms), at least five milliseconds (5 ms), at least six milliseconds (6 ms), at least seven milliseconds (7 ms), at least eight milliseconds (8 ms), at least nine milliseconds (9 ms), at least ten milliseconds (10 ms), at least eleven milliseconds (11 ms), at least twelve milliseconds (12 ms), at least thirteen milliseconds (13 ms), at least fourteen milliseconds (14 ms), and/or at least fifteen milliseconds (15 ms). In some examples, the weld time may be at most fifteen milliseconds (15 ms), at most fourteen milliseconds (14 ms), at most thirteen milliseconds (13 ms), at most twelve milliseconds (12 ms), at most eleven milliseconds (11 ms), at most ten milliseconds (10 ms), at most nine milliseconds (9 ms), at most eight milliseconds (8 ms), at most seven milliseconds (7 ms), at most six milliseconds (6 ms), at most five milliseconds (5 ms), at most four milliseconds (4 ms), at most three milliseconds (3 ms), at most two milliseconds (2 ms), at most one millisecond (1 ms), at most seventy-five hundredths of a millisecond (0.75 ms), and/or at most five tenths of a millisecond (0.5 ms).

In some examples where a joint is formed by laser welding the two members together the repetition frequency may be between five tenths to thirty hertz (0.5-30 Hz). In some examples, the repetition frequency may be at least five tenths of a hertz (0.5 Hz), at least one hertz (1 Hz), at least five hertz (5 Hz), at least ten hertz (10 Hz), at least fifteen hertz (15 Hz), at least twenty hertz (20 Hz), at least twenty-five hertz (25 Hz), and/or at least thirty hertz (30 Hz). In some examples, the repetition frequency may be at most thirty hertz (30 Hz), at most twenty-five hertz (25 Hz), at most twenty hertz (20 Hz), at most fifteen hertz (15 Hz), at most ten hertz (10 Hz), at most five hertz (5 Hz), at most one hertz (1 Hz), at most five tenths of a hertz (0.5 Hz).

In some examples where a joint is formed by laser welding the two members together the weld spot may be between two tenths to two millimeters (0.2-2.0 mm). In some examples, the weld spot may be at least two tenths of a millimeter (0.2 mm), at least three tenths of a millimeter (0.3 mm), at least four tenths of a millimeter (0.4 mm), at least four tenths of a millimeter (0.4 mm), at least five tenths of a millimeter (0.5 mm), at least six tenths of a millimeter (0.6 mm), at least seven tenths of a millimeter (0.7 mm), at least eight tenths of a millimeter (0.8 mm), at least nine tenths of a millimeter (0.9 mm), at least one millimeter (1 mm), at least one and one tenths of a millimeter (1.1 mm), at least one and two tenths of a millimeter (1.2 mm), at least one and three tenths millimeters (1.3 mm), at least one and four tenths millimeters (1.4 mm), at least one and five tenths millimeters (1.5 mm), at least one and six tenths millimeters (1.6 mm), at least one and seven tenths millimeters (1.7 mm), at least one and eight tenths millimeters (1.8 mm), at least one and nine tenths millimeters (1.9 mm), and/or at least two millimeters (2.0 mm). In some examples, the weld spot may be at most two tenths millimeters (0.2 mm), at most three tenths millimeters (0.3 mm), at most four tenths millimeters (0.4 mm), at most four tenths millimeters (0.4 mm), at most five tenths millimeters (0.5 mm), at most six tenths millimeters (0.6 mm), at most seven tenths millimeters (0.7 mm), at most eight tenths millimeters (0.8 mm), at most nine tenths millimeters (0.9 mm), at most 1 millimeter (1 mm), at most one and one tenths millimeters (1.1 mm), at most one and two tenths millimeters (1.2 mm), at most one and three tenths millimeters (1.3 mm), at most one and four tenths millimeters (1.4 mm), at most one and five tenths millimeters (1.5 mm), at most one and six tenths millimeters (1.6 mm), at most one and seven tenths millimeters (1.7 mm), at most one and eight tenths millimeters (1.8 mm), at most one and nine tenths millimeters (1.9 mm), and/or at most two millimeters (2.0 mm).

In some examples where a joint is formed by laser welding the two members together an inert gas may be supplied for between zero to ten seconds(s) (0-10 secs). In some examples, the inert gas may be supplied for at least one second (1 sec), at least two seconds (2 secs), at least three seconds (3 secs), at least four seconds (4 secs), at least five seconds (5 secs), at least six seconds (6 secs), at least seven seconds (7 secs), at least eight seconds (8 secs), at least nine seconds (9 secs), or at least ten seconds (10 secs). In some examples, the inert gas may be supplied for at most one second (1 sec), at most two seconds (2 secs), at most three seconds (3 secs), at most four seconds (4 secs), at most five seconds (5 secs), at most six seconds (6 secs), at most seven seconds (7 secs), at most eight seconds (8 secs), at most nine seconds (9 secs), or at most ten seconds (10 secs).

In some examples where a joint is formed by laser welding the two members together, the laser welder may have a peak power of between one tenth to three kilowatts (0.1-3 kW), the weld time (e.g., weld length) may be between five tenths to twelve milliseconds (0.5-12 ms), the repetition frequency may be between five tenths to six hertz (0.5-6 Hz), the weld spot may be between two tenths to two millimeters (0.2-2.0 mm), and an inert gas may be supplied for between zero to ten seconds(s) (0-10 secs). In some examples where a joint is formed by laser welding the two members together, the laser welder may have a peak power of between six tenths to one and one tenth of a kilowatt (0.6-1.1 kW), the weld time (e.g., weld length) may be between two tenths to one millisecond (0.2-1.0 ms), the repetition frequency may be between two to four hertz (2-4 Hz), the weld spot may be two tenths of a millimeter (0.2 mm), and an inert gas may be supplied for between one to four seconds(s) (1-4 secs). Below is a table of both the aforementioned parameters and core sizes for the two conductive members joined at the joint (copper and molybdenum).

TABLE 2

| Cu Core Size (inches) | Mo Core Size (inches) | Power (kilowatts) | Time (milliseconds) | Freq (hertz) | Spot (millimeter) | Gas (seconds) |
|---|---|---|---|---|---|---|
| .005 in | .003 in | .6 kW | .4 ms | 2 Hz | .2 mm | 2 s |
| .005 in | .004 in | .6 kW | .6 ms | 3 Hz | .2 mm | 3 s |
| .007 in | .005 in | 1.1 kW | .2 ms | 4 Hz | .2 mm | 2 s |
| .007 in | .007 in | .8 kW | 1 ms | 4 Hz | .2 mm | 1 s |

While the examples shown in the table above are for copper and molybdenum conductive members, it should be understood that other materials may be used to form laser welded electrical joints. For instance, one or more electrical joints may be formed between copper and tungsten.

In some examples, forming the one or more electrical joints includes soldering the first conductive member to the second conductive member. Forming the one or more joints by soldering the first conductive member to the second conductive member may include coating or plating at least a portion of the second conductive member with a coating or plating that facilitates a soldered connection with the first conductive member. In some examples, the coating or plating may include the first material (e.g., copper). The coating or plating may include a nickel-copper coating or plating which may include between zero to ten microns (0-10 μm) of nickel and between one hundred to two hundred microns (100-200 μm) of copper. In some examples, the coating or plating may include between 0% and 5% nickel and between 100% and 95% copper. In some examples, the coating or plating may include between 0% and 10% nickel and between 100% and 90% copper. In some examples, the ratio of copper to nickel of the plating may be between 200 to 1 and 10 to 1. In some examples, the coating or plating may be a nickel-chromium plating (e.g., 50% nickel, 50% chromium). Additionally, or alternatively, forming the one or more joints by soldering the first conductive member to the second conductive member may include coating or plating at least a portion of the first conductive member with a coating or plating that facilitates a soldered connection with the second conductive member (e.g., a coating or plating including the second material). In some examples, forming a soldered joint includes overlapping the conductive member 214 with conductive member 218 by between one millimeter (1 mm) and five millimeters (5 mm) (e.g., one millimeter (1 mm), two millimeters (2 mm), three millimeters (3 mm)) and soldering a joint. In some examples, the joint may additionally or alternatively be formed by swaging.

In some examples, forming the one or more electrical joints includes applying an adhesive to adhere the first conductive member to the second conductive member. In some examples, forming the one or more electrical joints includes cleaning a surface (e.g., to remove oil, grease, dirt, etc.) of first conductive member and/or the second conductive member prior to applying an adhesive. In some examples, forming the one or more electrical joints includes sanding a surface of first conductive member and/or the second conductive member prior to applying an adhesive. In some examples, forming the one or more electrical joints includes using an outer conductive sleeve to capture the first conductive member and the second conductive member prior to applying a conductive adhesive to the conductive sleeve, first conductive member, and the second conductive member. In some examples, forming the one or more electrical joints includes performing tensile tests to make sure parts are bonded properly and/or performing a resistance test to ensure low resistance/high conductivity of one or more subassemblies of the joints. In some examples, a proper joint does not experience any arcing, heating, or failure of the joint during testing.

It should be understood that the blocks (e.g., 302, 304, and 306) of the method 300 are not necessarily performed in the order presented. For instance, the electrical joints may be formed prior to securing the first and/or second conductive member to the catheter body, the first conductive member may be secured to the catheter body before, after, or simultaneously with the second member, and so on.

Figure 4A:
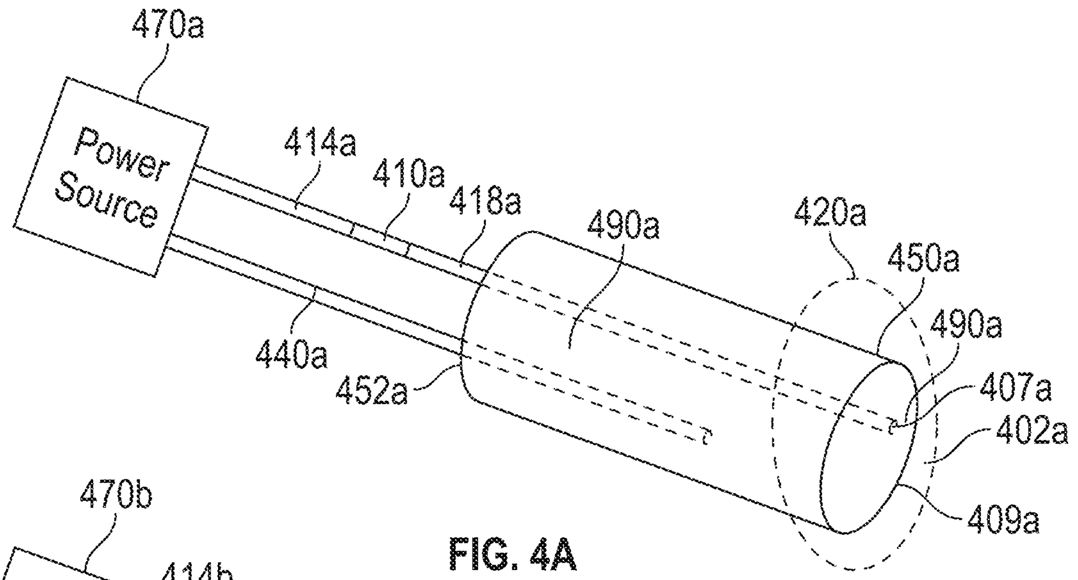
FIG. 4A illustrates an exemplary shock wave emitter and an electrical joint positioned proximally of the shock wave emitter, according to some examples.
Figure 4B:
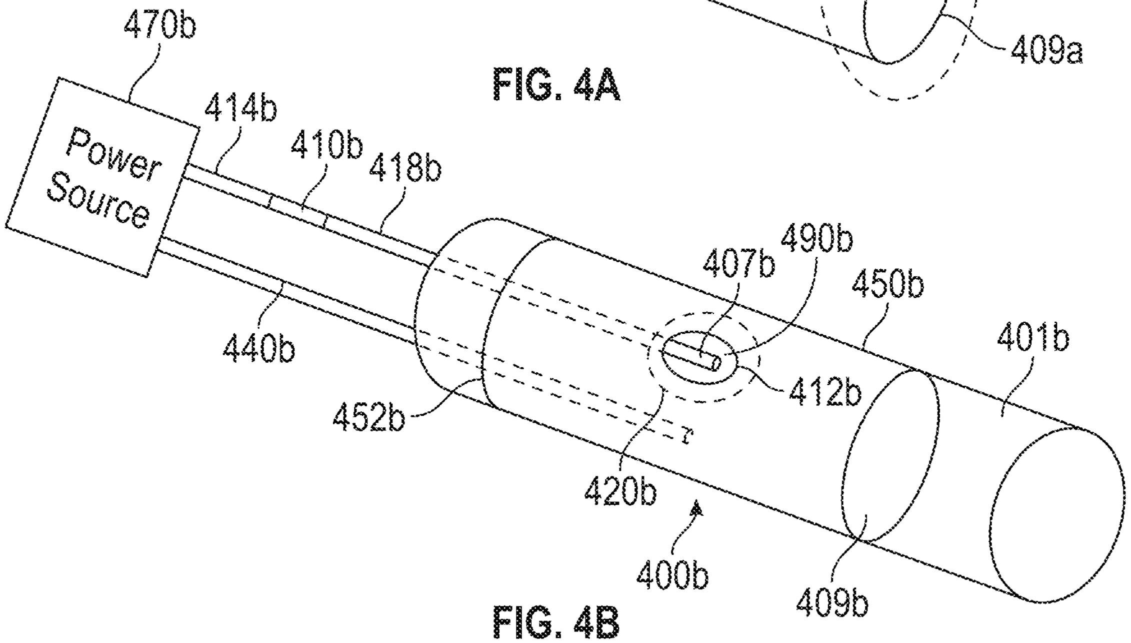
FIG. 4B illustrates another exemplary shock wave emitter and an electrical joint positioned proximally of the shock wave emitter, according to some examples.
Figure 4C:
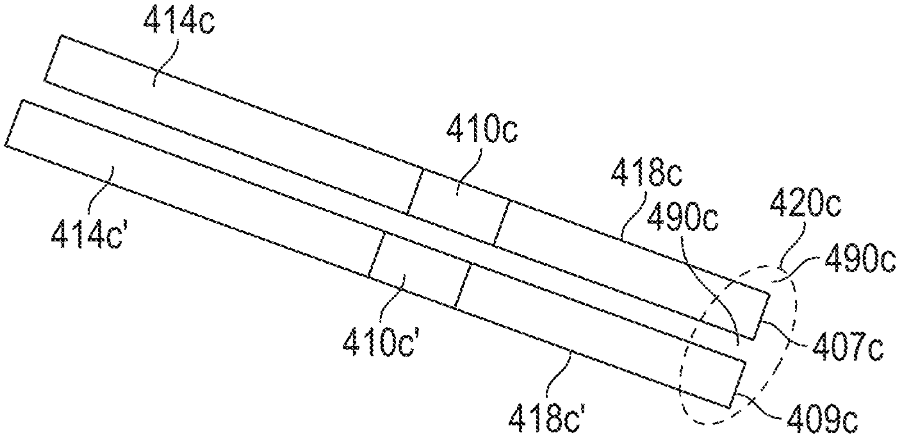
FIG. 4C illustrates another exemplary shock wave emitter and an electrical joint positioned proximally of the shock wave emitter, according to some examples.

The electrical joints described above may be implemented on any shock wave generating catheter to facilitate use of durable materials such as molybdenum as electrodes for shock wave emitters. For instance, any number of different shock wave emitter configurations are possible in addition to, or in place of, those described above with reference to FIG. 2. The electrical joints described above may be implemented on shock wave generating catheters that include forward firing emitters, radially firing emitters, emitters that include an exposed end of a wire separated from a conductive band by a spark gap, emitters that include an exposed end of two wires separated from one another by a spark gap, and so on. A variety of exemplary shock wave emitter configurations including electrodes formed from a material such as molybdenum that is electrically coupled to a material such as copper using one or more electrical joints are illustrated in FIGS. 4A-4C. A person having skill in the art would understand that the depicted configurations are only exemplary and a variety of alternative shock wave emitter configurations are within the scope of this disclosure.

FIG. 4A illustrates an exemplary shock wave emitter 420*a* that includes a conductive emitter band 450*a* spaced apart from an exposed end 407*a* of a conductive member 418*a* by a spark gap. The exposed end 407*a* and conductive emitter band 450*a* can be positioned relative to one another such that when a sufficiently high voltage is applied across the spark gap 490*a* separating the exposed end 407*a* and conductive emitter band 450*a*, a shock wave is generated. In some examples, the exemplary shock wave emitter depicted in FIG. 4A may be positioned at a distal end of a catheter and utilized to generate shock waves that propagate distally of the distal end of the catheter, for instance, as described in U.S. patent application Ser. No. 18/524,575, which is incorporated herein by reference in its entirety. Shock wave emitter 420*a* may be electrically coupled to one or more additional shock wave emitters, e.g., by extending conductive members between adjacent emitter bands to conduct current from one emitter band to the next in series. A conductive member 440*a* may be electrically connected to emitter band 450*a*. Conductive member 440*a* may also be electrically connected to a return terminal at a power source 470*a* such that when one or more shock waves are emitted using shock wave emitter 420*a*, conductive member 440*a* serves as a return wire.

In some examples, conductive emitter band 450*a* includes a proximal end 452*a* and a distal end 409*a*. A portion of conductive member 418*a* including exposed end 407*a* may be positioned such that it is at least partially enclosed within conductive emitter band 450*a*. Conductive member 418*a* may extend from the distal end 409*a* of emitter band 450*a* and exit the emitter band 450*a* at the its proximal end 452*a*. Conductive member 418*a* may further extend to an electrical joint 410*a* that electrically couples conductive member 418*a* to conductive member 414*a*. Conductive member 414*a* may be formed of a first, more conductive material (e.g., copper), and conductive member 418*a* may be formed of a second, more durable material (e.g., molybdenum), as described throughout. Electrical joint 410*a* may include any of the features and be formed by any of the methods described above.

FIG. 4B illustrates an exemplary shock wave emitter 420*b* that includes a conductive emitter band 450*b* positioned such that it surrounds at least a portion of a catheter body 401*b* of catheter 400. Shock wave emitter 420*b* includes an exposed end 407*b* of a conductive member (e.g., an insulated wire) 418*b* positioned adjacent to emitter band 450*b* and spaced apart from the emitter band 450*b* by a spark gap 490*b* such that when a sufficiently high voltage is applied across the spark gap separating the exposed end 407*b* and conductive emitter band 450*b*, a shock wave is generated. In some examples, exposed end 407*b* of a conductive member 418*b* is positioned such that it is aligned with an opening 412*b* of emitter band 450*b* that forms the spark gap between exposed end 407*b* and emitter band 450*b*. In some examples, additional conductive members may be positioned adjacent to conductive emitter band 450*b* to form additional shock wave emitters about the circumference of the band. A conductive member 440*b* may be electrically connected to emitter band 450*b*. Conductive member 440*b* may also be electrically connected to a return terminal at a power source 470*b* such that when one or more shock waves are emitted using shock wave emitter 420*b*, conductive member 440*b* serves as a return wire.

In some examples, conductive emitter band 450*b* includes a proximal end 452*b* and a distal end 409*b*. A portion of conductive member 418*b* including exposed end 407*b* may be positioned such that it is at least partially enclosed within conductive emitter band 450*b*. Conductive member 418*b* may extend from opening 412*b* of emitter band 450*b* and exit the emitter band 450*b* at the its proximal end 452*b*. Conductive member 418*b* may further extend to an electrical joint 410*b* that electrically couples conductive member 418*b* to conductive member 414*b*. Conductive member 414*b* may be formed of a first, more conductive material (e.g., copper), and conductive member 418*b* may be formed of a second, more durable material (e.g., molybdenum), as described throughout this disclosure. Electrical joint 410*b* may include any of the features and be formed by any of the methods described above.

FIG. 4C illustrates an exemplary shock wave emitter 420*c* that includes an exposed end 407*c* of a first conductive member 418*c* (e.g., a first insulated wire) separated by a spark gap 490*c* from an exposed end 409*c* of a second conductive member 418*c*' (e.g., a second insulated wire) such that when a sufficiently high voltage is applied across the spark gap separating the exposed end 407*c* from exposed end 409*c*, a shock wave is generated. In some examples, conductive members 418*c* and 418*c*' may extend away from the shock wave emitter 420*c* to a respective electrical joint 410*c* and 410*c*'. Electrical joint 410*c* electrically couples conductive member 418*c* to conductive member 414*c*, and electrical joint 410*c*' electrically couples conductive member 418*c*' to conductive member 414*c*'. Conductive members 414*c* and 414*c*' may be formed of a first, more conductive material (e.g., copper), and conductive members 418*c* and 418*c*' may be formed of a second, more durable material (e.g., molybdenum), as described throughout this disclosure. Electrical joints 410*c* and 414*c*' may include any of the features and be formed by any of the methods described above.

Figure 5A:
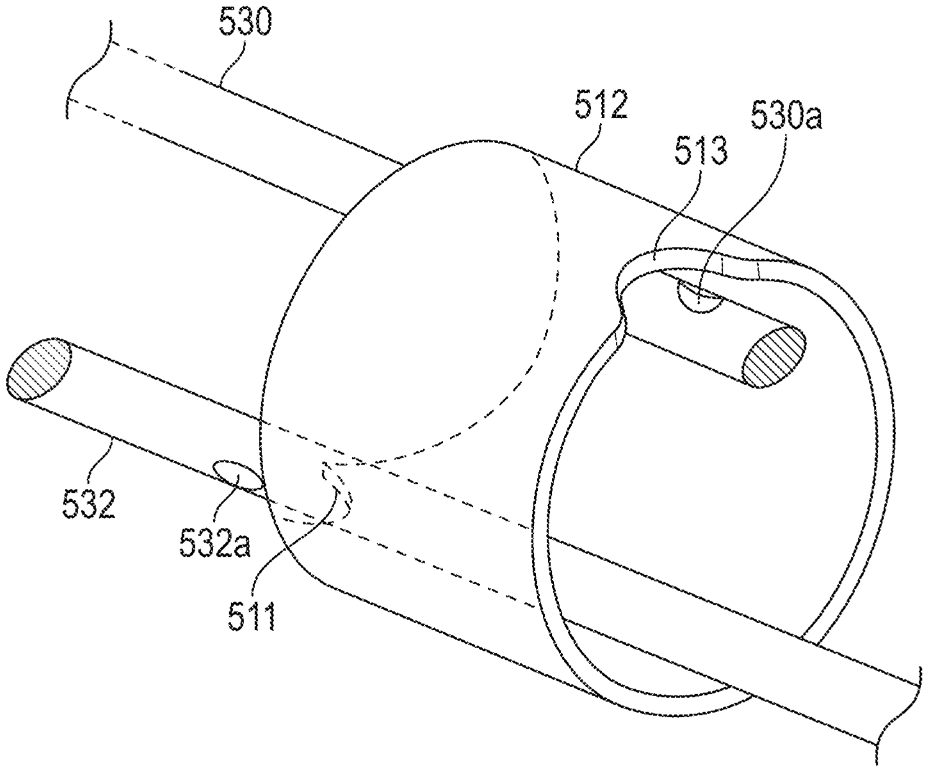
FIG. 5A illustrates an emitter sheath separated from two electrodes by respective spark gaps, according to some examples.

FIG. 5A illustrates, as part of a shock wave catheter, an exemplary shock wave emitter that includes a first electrode formed at a side edge of a conductive band 512, according to aspects of the disclosure. A conductive member 530 including a refractory metal and having an exposed region 530*a* (e.g., an end or an exposed side) may make up the second electrode of the electrode pair. The exposed region 530*a* may be spaced apart from the side edge of the conductive band 512 to provide a spark gap, where shock waves are generated. The side edge 513 of the conductive band may include a cut out region (e.g., an arcuate cut-out region) that at least partially surrounds the exposed region of the conductive member. This electrode configuration may contribute to generating reproducible shock waves that propagate substantially laterally (i.e., transverse to a distal-proximal axis). The conductive member 530 may extend a relatively short distance and be electrically connected by any of the methods described above to a more conductive and/or more flexible member that extends along a length of the catheter.

In a similar manner, a portion of the insulated wire 532 is removed to form a second inner electrode 532*a*. Specifically, a portion of the insulating layer of the wire 532 is removed near the proximal end of the wire 532 to expose an electrically conductive wire portion along the length of the wire, forming the second inner electrode 532*a*. The second inner electrode 532*a* may also include a refractory metal, as described herein. As shown, the second inner electrode 532*a* is adjacent to, but not in contact with, a proximal side edge 511 of the first conductive sheath 512. Further, the first inner electrode 530*a* and the second inner electrode 532*a* are positioned circumferentially 180 degrees from each other. In operation, the first conductive sheath 512 acts as an outer electrode, and a second shock wave is created across the second inner electrode 432*a* and the proximal side edge 511 of the first conductive sheath 512.

Figure 5B:
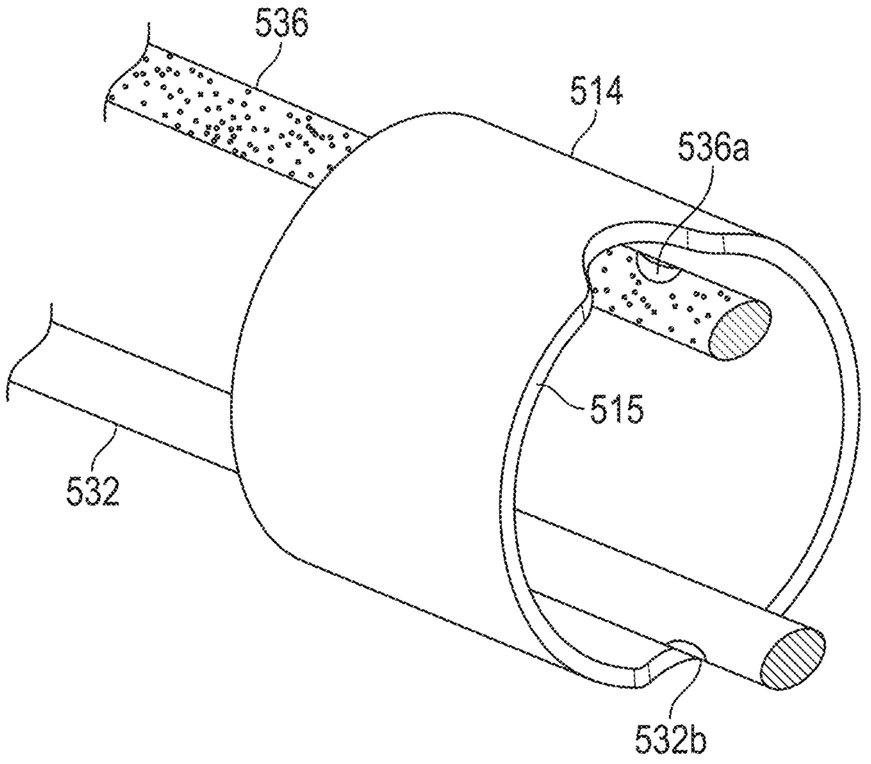
FIG. 5B illustrates another emitter sheath separated from two electrodes by respective spark gaps, according to some examples.

FIG. 5B illustrates a third inner electrode 532*b* formed on the insulated wire 532 and a fourth inner electrode 536*a* formed on insulated wire 536 in a similar manner as described above with reference to FIG. 5A. As depicted, the third inner electrode 532*b* is formed near the distal end of the insulated wire 532 and is adjacent to, but not in contact with, a distal side edge 515 of the second conductive sheath 514. The fourth inner electrode 536*a* is formed near the distal end of the insulated wire 536 and is adjacent to, but not in contact with, the same distal side edge 515 of the second conductive sheath 514. The third and/or fourth inner electrodes 532*b* and 536*a* may include a refractory metal, as described herein. In operation, the second conductive sheath 514 acts as an outer electrode, a third shock wave is created across the third electrode 532*b* and the distal side edge 515, and a fourth shock wave is created across the fourth electrode 536*a* and the distal side edge 515.

Figure 6:
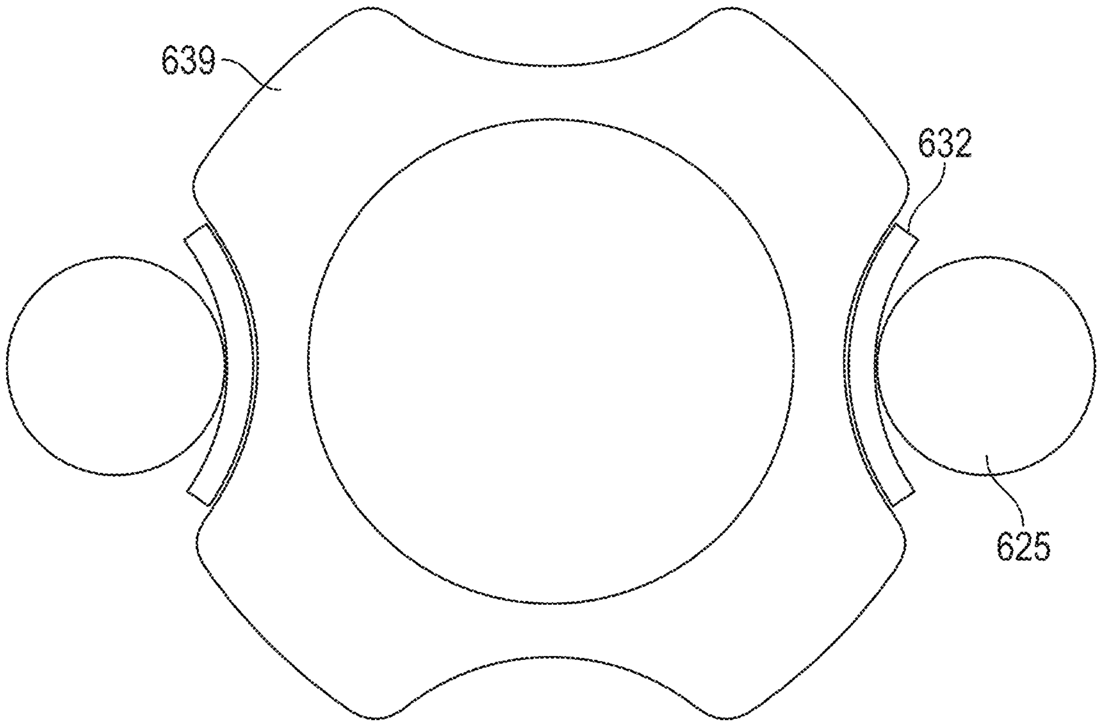
FIG. 6 illustrates a cross-sectional view of an exemplary catheter including a protective layer, according to some examples.
Figure 7A:
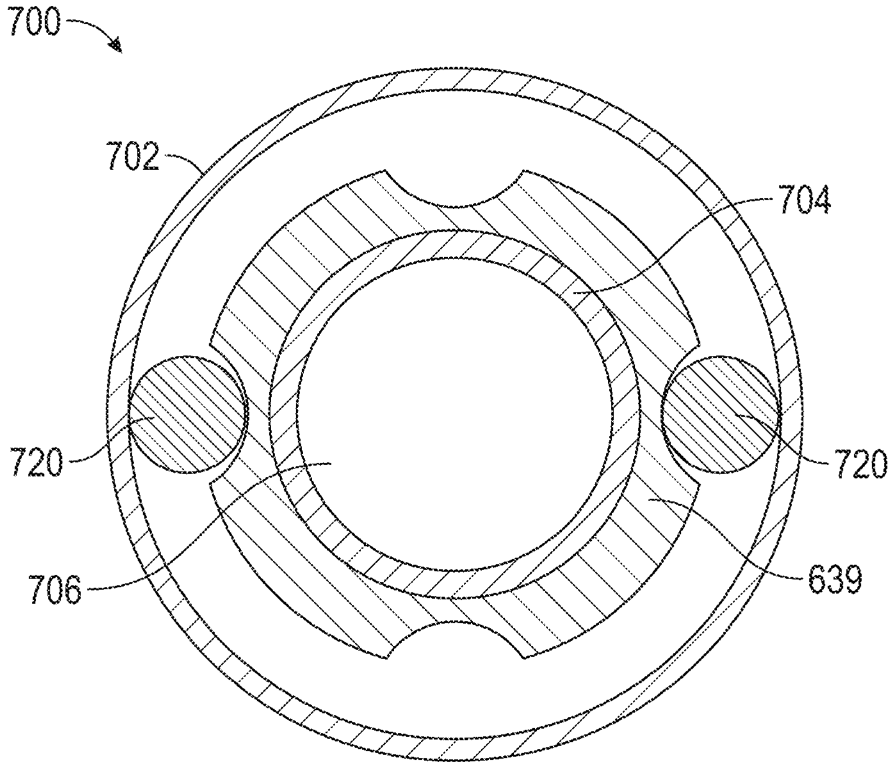
FIG. 7A illustrates a catheter having an outer layer that at least partially surrounds conductive members and keeps the conductive members in contact with the catheter body, according to some examples.
Figure 7B:
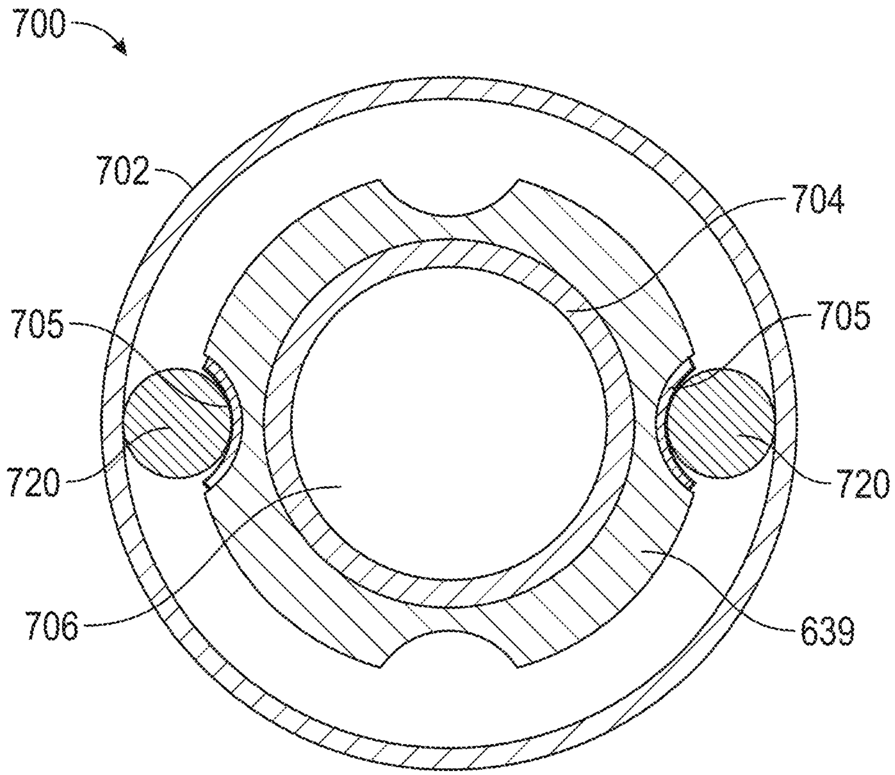
FIG. 7B illustrates a catheter having an inner layer positioned between conductive members and the catheter body, according to some examples.

In some aspects, the longevity of the catheter may be extended by including one or more protective layers. FIG. 6 illustrates a cross-sectional view of an exemplary catheter including a protective layer, according to some examples. The catheter may include a protective layer 632 located between a conductive member 625 and the catheter body 639. In some examples, the protective layer may additionally or alternatively (as shown in FIG. 7A) lie within a lumen of catheter body 639 (second inner layer 704) and/or around the catheter body 339 (outer layer 702 surrounding at least a portion of the wires and/or first inner layer 705 positioned between the conductive members 720 and catheter body 639 as shown in FIG. 7B). In some aspects, the protective layer 632 may serve as an additional layer of insulation to prevent or reduce pitting inside the lumen of catheter body 639 from the heat and pressures associated with shock wave generation. One non-limiting example type of a protective layer is a polymer layer (e.g., a polyimide layer). In some examples, the protective layer may be made of an electrically insulating material. In some examples, the protective layer may be made of a material having a low thermal conductivity. The protective layer 632 may improve sonic output and longevity. As shown in the figure, the conductive member 625 may have a circular profile.

FIG. 7A also illustrates a catheter 700 having an outer layer 702 that at least partially surrounds the conductive members 720 and keeps the conductive members 720 in contact with the catheter body 639. The outer layer 702 may be made of an electrically insulating polymer (e.g., polyether block amide (peba) or nylon). In various embodiments, the outer protective layer 702 does not surround one or more shock wave emitters positioned on the catheter body. In various embodiments, the outer protective layer 702 surrounds the conductive members 625 and includes openings (e.g., holes, slits, gaps) to expose shock wave emitters to conductive fluid. In some examples, the inner protective layer 706 may be formed of the same material as the outer protective layer.

Figure 8:
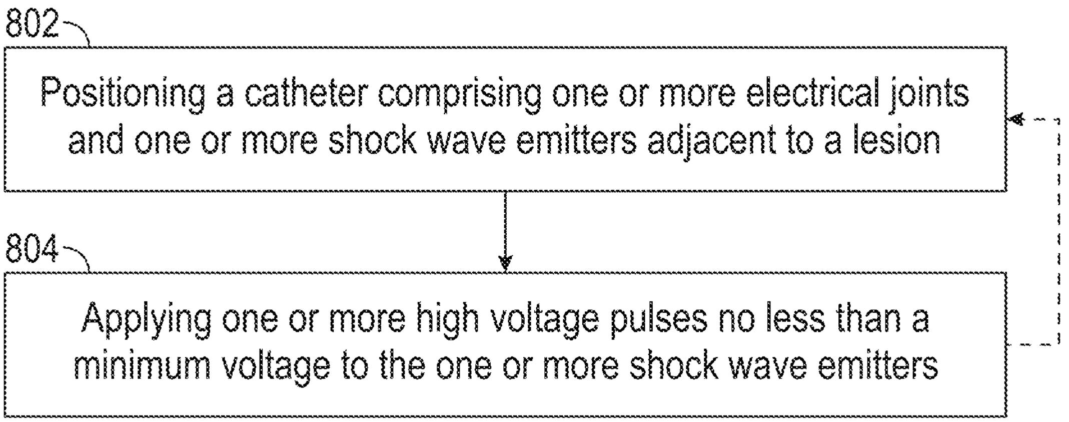
FIG. 8 illustrates a method for iteratively generating shock waves by applying high voltage pulses to shock wave emitters, according to some examples.
Figure 9:
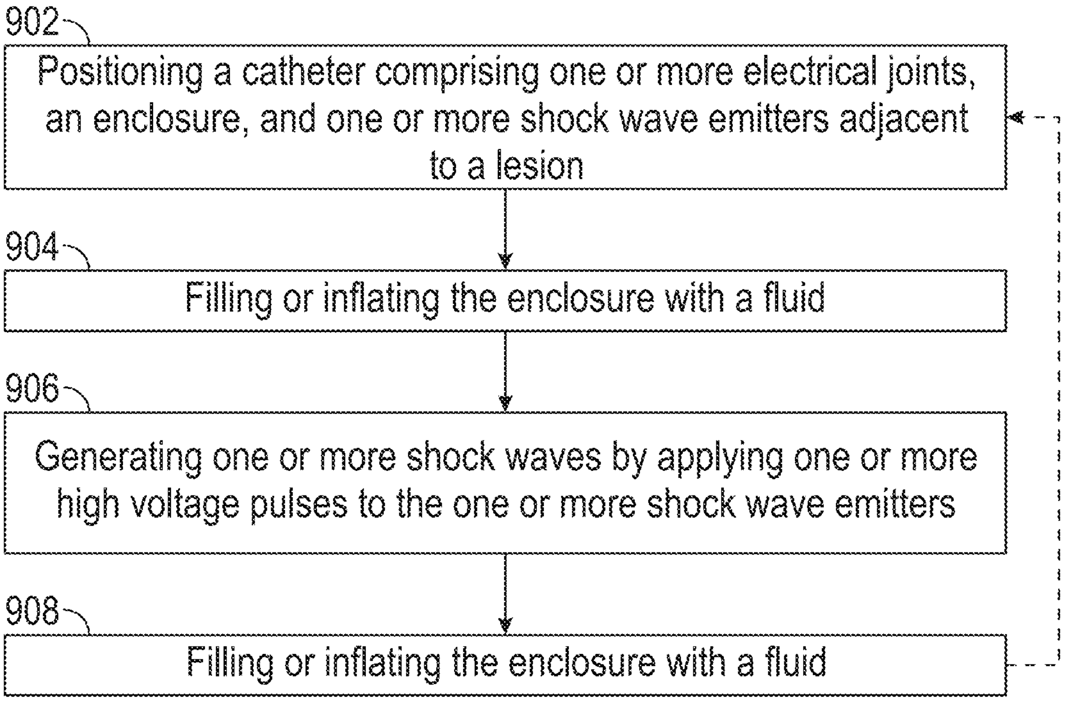
FIG. 9 illustrates a method for iteratively generating shock waves using a catheter that includes one or more electrical joints, an enclosure, and one or more shock wave emitters, according to some examples.

In some examples, the catheters and shock wave emitters described above are used for treating lesions including calcified regions of vasculature, a thrombus or an occlusion in vasculature, arteriosclerotic plaque, or a lesion in some other body lumen, such as a kidney stone in a ureter. FIGS. 8 and 9 described in detail below illustrate exemplary methods for using the shock wave generating catheters described herein for treating such lesions.

FIG. 8 illustrates a method for iteratively applying high voltage pulses to shock wave emitters according to some examples. At block 802, a catheter including one or more electrical joints and one or more shock wave emitters is positioned adjacent to a lesion (e.g., a calcification within a body lumen. At block 804, one or more high voltage pulses no less than a minimum voltage are applied to the one or more shock wave emitters. In some examples, after applying one or more high voltage pulses, blocks 802 and 804 may optionally be repeated, repositioning the catheter adjacent to the lesion and applying additional high voltage pulses until the lesion is successfully treated.

In some examples, the high voltage pulses are applied at a voltage of at least at least one kilovolt (1 kV), at least two kilovolts (2 kV), at least three kilovolts (3 kV), at least three kilovolts (4 kV), at least five kilovolts (5 kV), at least six kilovolts (6 kV), at least seven kilovolts (7 kV), at least eight kilovolts (8 kV), at least nine kilovolts (9 kV), at least ten kilovolts (10 kV), at least eleven kilovolts (11 kV), at least twelve kilovolts (12 kV), at least thirteen kilovolts (13 kV), at least fourteen kilovolts (14 kV), at least fifteen kilovolts (15 kV), at least sixteen kilovolts (16 kV), at least seventeen kilovolts (17 kV), at least eighteen kilovolts (18 kV), at least nineteen kilovolts (19 kV), at least twenty kilovolts (20 kV), and/or at least thirty kilovolts (30 kV). The high voltage pulses may be no more than thirty kilovolts (30 kV), no more than twenty kilovolts (20 kV), no more than nineteen kilovolts (19 kV), no more than eighteen kilovolts (18 kV), no more than seventeen kilovolts (17 kV), no more than sixteen kilovolts (16 kV), no more than fifteen kilovolts (15 kV), no more than fourteen kilovolts (14 kV), no more than thirteen kilovolts (13 kV), no more than twelve kilovolts (12 kV), no more than eleven kilovolts (11 kV), no more than ten kilovolts (10 kV), no more than nine kilovolts (9 kV), no more than eight kilovolts (8 kV), no more than seven kilovolts (7 kV), no more than six kilovolts (6 kV), no more than five kilovolts (5 kV), no more than four kilovolts (4 kV), no more than three kilovolts (3 kV), no more than two kilovolts (2 kV), and/or no more than one kilovolt (1 kV).

The voltage pulses may be applied at a rate of a rate of between 1 Hz and 50 Hz, including one hertz (1 Hz) and fifty hertz (50 Hz). Shock wave energy generator 530 may be configured to deliver the voltage pulses at a rate of a rate of up to one hundred hertz (100 Hz), up to ninety hertz (90 Hz), up to eighty hertz (80 Hz), up to seventy hertz (70 Hz), up to sixty hertz (60 Hz), up to fifty hertz (50 Hz), up to forty hertz (40 Hz), up to thirty hertz (30 Hz), up to twenty hertz (20 Hz), and/or up to ten hertz (10 Hz). Shock wave energy generator 530 may be configured to deliver the voltage pulses at a rate of at least ten hertz (10 Hz), at least twenty hertz (20 Hz), at least thirty hertz (30 Hz), at least forty hertz (40 Hz), at least fifty hertz (50 Hz), at least sixty hertz (60 Hz), at least seventy hertz (70 Hz), at least eighty hertz (80 Hz), at least ninety hertz (90 Hz), and/or at least one hundred hertz (100 Hz). In some embodiments, voltage pulses may be delivered as packets of sub-pulses having frequencies up to ten hertz (10 kHz), where the packets are delivered at a frequency of one hertz (1 Hz) to ten hertz (10 Hz).

FIG. 9 illustrates an exemplary method for iteratively generating shock waves using a catheter that includes one or more electrical joints, an enclosure, and one or more shock wave emitters adjacent to a lesion. At block 902, a catheter including one or more electrical joints, an enclosure, and one or more shock wave emitters are positioned adjacent to a lesion (e.g., within a body lumen). The one or more electrical joints and shock wave emitters may include any of the features described throughout (e.g., with respect to FIGS. 1-4C). The enclosure may be an acoustically transparent enclosure (e.g., an angioplasty balloon that is positioned to at least partially surround one or more of the one or more shock wave emitters). The enclosure may be configured to be filled and/or inflated with a conductive fluid as described with reference to FIG. 1.

At block 904, the enclosure may be filled or inflated with a fluid such as a contrastive agent or other conductive fluid, and at block 906, one or more shock waves may be generated by applying one or more high voltage pulses to the one or more shock wave emitters. The high voltage pulses may be applied at any of the voltages and/or frequencies described above with reference to FIG. 8. At block 908, the enclosure may be filled or inflated following the generation of one or more shock waves. The conductive fluid may aid in cooling the device and dissipating heat generated during the formation of vapor bubbles that result from shock wave generation. Blocks 902-908 may optionally be repeated as needed until the lesion is successfully treated.

Figure 10:
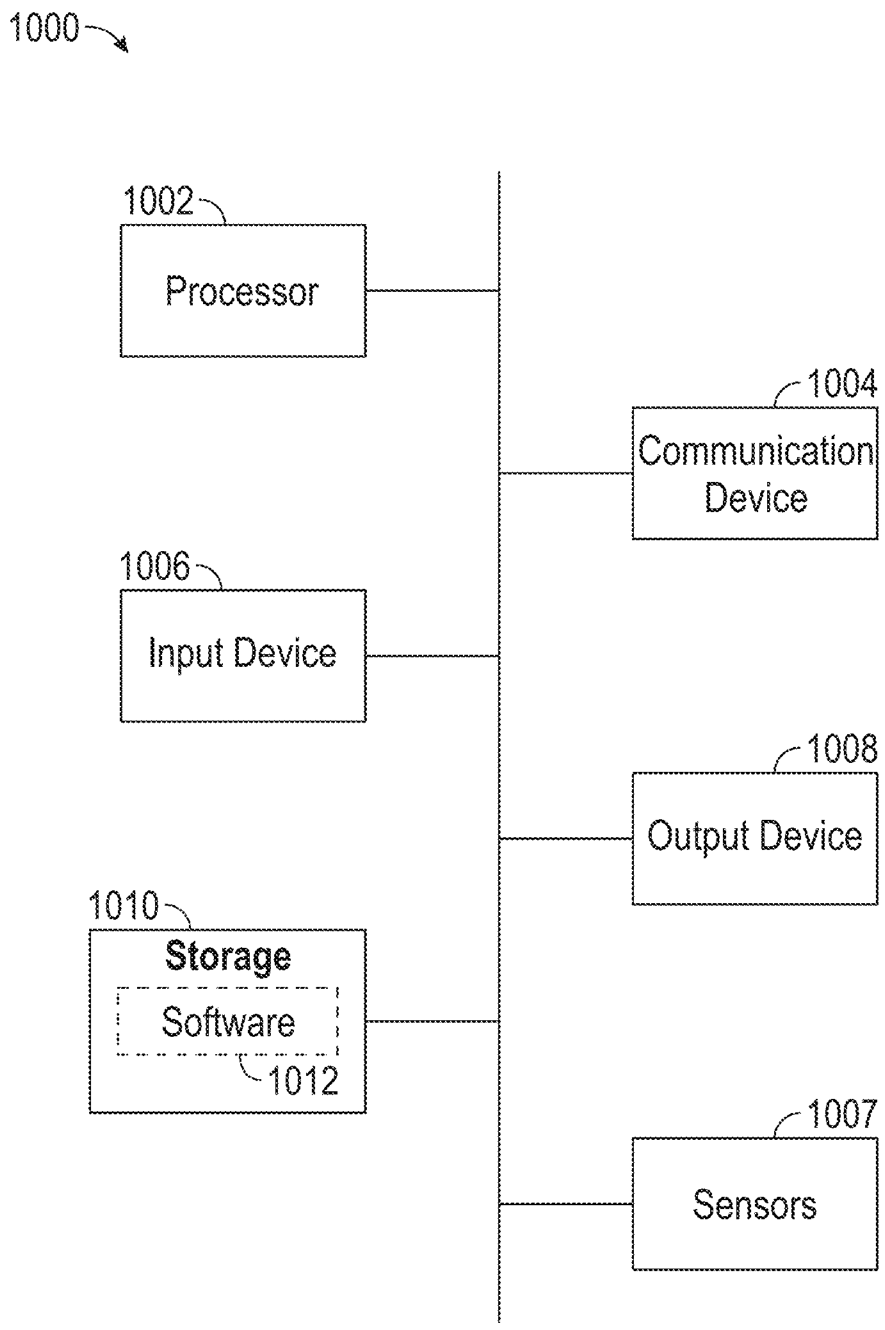
FIG. 10 illustrates an exemplary computing system, according to some examples.

FIG. 10 depicts an exemplary computing device 1000 which may form part of the system 100 described above and may be used for performing various steps of the methods described herein, in accordance with one or more examples of the disclosure. Device 1000 can be a host computer connected to a network. Device 1000 can be a client computer or a server. As shown in FIG. 10, device 1000 can be any suitable type of microprocessor-based device, such as a personal computer, workstation, server, or handheld computing device (i.e., a portable electronic device) such as a phone or tablet. The device can include, for example, one or more of processors 1002, input device 1006, sensor device 1007, output device 1008, storage 1010, and communication device 1004. Input device 1006 and output device 1008 can generally correspond to those described above and can either be connectable or integrated with the computer.

Input device 1006 can be any suitable device that provides directed input, such as a touch screen, keyboard or keypad, mouse, or voice-recognition device, in other words, input or directions provided or initiated by a user. Sensor device 1007 can be one or more of any suitable sensor devices, such as a pressure sensor, a thermal sensor, an electrical sensor (e.g., current, voltage, resistance, and/or impedance sensors), or a visualization element. Output device 1008 can be any suitable device that provides output, such as a touch screen, haptics device, or speaker. Storage 1010 can be any suitable device that provides storage, such as an electrical, magnetic, or optical memory, including a RAM, cache, hard drive, or removable storage disk. Communication device 1004 can include any suitable device capable of transmitting and receiving signals over a network, such as a network interface chip or device. The components of the computer can be connected in any suitable manner, such as via a physical bus or wirelessly.

Sensor devices 1007 can provide feedback to an operator using device 1000 by measuring parameters in the surrounding environment and thereby indicating a status of a shock wave catheter device such as catheter 100 connected to computing device 1000, and further providing for guidance on what further steps the operator may decide to implement a shock wave catheter device such as catheter 100 connected to computing device 1000. For example, in implementations where sensor devices 1007 include pressure sensors, a slight decrease in pressure may indicate success at cracking a calcified lesion, due to the fact that an expandable member (e.g., enclosure 120) surrounding shock wave emitters is able to further expand without changing the volume of fluid within the expandable member. Further, a significant decrease in pressure may indicate a rupture failure mode where the expandable member has lost seal and fluid volume, and thus guiding toward withdrawal of the device (e.g., device 100). In implementations where the sensor devices include a visualization element, an operator of a catheter device such as catheter 100 may be able to more clearly understand where the catheter is located relative to a target lesion or anatomy, prior to, during, and after delivering therapy.

In some embodiments, sensor device 1007 includes surface electrodes of an electrocardiograph to synchronize a shock wave to the "R" wave for treating vessels near the heart. Sensor device 1007 may include an R-wave detector and a controller to control the high voltage switch. Mechanical shocks can stimulate heart muscle and could lead to an arrhythmia. While it is unlikely that shock waves of such short duration as contemplated herein would stimulate the heart by synchronizing the pulses (or bursts of pulses) with the R-wave, an additional degree of safety may be provided when used on vessels of the heart or near the heart. In implementations where shock waves are generated from open unenclosed emitters, synchronization to the R-wave would significantly improve the safety against unwanted arrhythmias.

Software 1012, which can be stored in storage 1010 and executed by processor 1002, can include, for example, the programming that embodies the functionality of the present disclosure (e.g., as embodied in the devices as described above). Software 1012 can also be stored and/or transported within any non-transitory computer-readable storage medium for use by, or in connection with, an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 1010, that can contain or store programming for use by, or in connection with, an instruction execution system, apparatus, or device. Software 1012 can also be propagated within any transport medium for use by, or in connection with, an instruction execution system, apparatus, or device, such as those described above, that can fetch instructions associated with the software from the instruction execution system, apparatus, or device and execute the instructions. In the context of this disclosure, a transport medium can be any medium that can communicate, propagate, or transport programming for use by, or in connection with, an instruction execution system, apparatus, or device. The transport-readable medium can include, but is not limited to, an electronic, magnetic, optical, electromagnetic, or infrared wired or wireless propagation medium.

Device 1000 may be connected to a network, which can be any suitable type of interconnected communication system. The network can implement any suitable communication protocols and can be secured by any suitable security protocols. The network can comprise network links of any suitable arrangement that can implement the transmission and reception of network signals, such as wireless network connections, T1 or T3 lines, cable networks, DSL, or telephone lines. Device 1000 can implement any operating system suitable for operating on the network. Software 1012 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Although the electrode assemblies and catheter devices described herein have been discussed primarily in the context of treating coronary occlusions, such as lesions in vasculature, the electrode assemblies and catheters herein can be used for a variety of occlusions, such as occlusions in the peripheral vasculature (e.g., above-the-knee, below-the-knee, iliac, carotid, etc.). For further examples, similar designs may be used for treating soft tissues, such as cancer and tumors (i.e., non-thermal ablation methods), blood clots, fibroids, cysts, organs, scar and fibrotic tissue removal, or other tissue destruction and removal. Electrode assembly and catheter designs could also be used for neurostimulation treatments, targeted drug delivery, treatments of tumors in body lumens (e.g., tumors in blood vessels, the esophagus, intestines, stomach, or vagina), wound treatment, non-surgical removal and destruction of tissue, or used in place of thermal treatments or cauterization for venous insufficiency and fallopian ligation (i.e., for permanent female contraception).

In one or more examples, the electrode assemblies and catheters described herein could also be used for tissue engineering methods, for instance, for mechanical tissue decellularization to create a bioactive scaffold in which new cells (e.g., exogenous or endogenous cells) can replace the old cells; introducing porosity to a site to improve cellular retention, cellular infiltration/migration, and diffusion of nutrients and signaling molecules to promote angiogenesis, cellular proliferation, and tissue regeneration similar to cell replacement therapy. Such tissue engineering methods may be useful for treating ischemic heart disease, fibrotic liver, fibrotic bowel, and traumatic spinal cord injury (SCI). For instance, for the treatment of spinal cord injury, the devices and assemblies described herein could facilitate the removal of scarred spinal cord tissue, which acts like a barrier for neuronal reconnection, before the injection of an anti-inflammatory hydrogel loaded with lentivirus to genetically engineer the spinal cord neurons to regenerate.

The elements and features of the exemplary electrode assemblies and catheters discussed above may be rearranged, recombined, and modified, without departing from the present invention. Furthermore, numerical designators such as "first", "second", "third", "fourth", etc. are merely descriptive and do not indicate a relative order, location, or identity of elements or features described by the designators. For instance, a "first" shock wave may be immediately succeeded by a "third" shock wave, which is then succeeded by a "second" shock wave. As another example, a "third" emitter may be used to generate a "first" shock wave and vice versa. Accordingly, numerical designators of various elements and features are not intended to limit the disclosure and may be modified and interchanged without departing from the subject invention.

It should be noted that the elements and features of the example catheters illustrated throughout this specification and drawings may be rearranged, recombined, and modified without departing from the present invention. For instance, while this specification and drawings describe and illustrate catheters having several example balloon designs, the present disclosure is intended to include catheters having a variety of balloon configurations. The number, placement, and spacing of the electrode pairs of the shock wave generators can be modified without departing from the subject invention. Further, the number, placement, and spacing of balloons of catheters can be modified without departing from the subject invention.

It should be understood that the foregoing is only illustrative of the principles of the invention, and that various modifications, alterations and combinations can be made by those skilled in the art without departing from the scope and spirit of the invention. Any of the variations of the various catheters disclosed herein can include features described by any other catheters or combination of catheters herein. Furthermore, any of the methods can be used with any of the catheters disclosed. Accordingly, it is not intended that the invention be limited, except as by the appended claims.

The invention claimed is:

1. A method of forming a catheter comprising one or more electrical joints configured to electrically couple a first conductive member to a second conductive member, the method comprising:

securing a first conductive member comprising a first material to a catheter body;

securing a second conductive member comprising a second material different from the first material to the catheter body at a location distal of the first conductive member on the catheter body; and forming one or more electrical joints for electrically coupling and joining the first conductive member and the second conductive member, wherein forming one or more electrical joints comprises:

applying pressure to the first conductive member and the second conductive member;

passing current through the first conductive member, the second conductive member, or both to generate heat; and melting at least one of the first conductive member and the second conductive member to join the first conductive member and the second conductive member together.

2. The method of claim 1, wherein the current is between 1 ampere and 5 amperes.

3. The method of claim 1, wherein applying pressure to the first conductive member and the second conductive member comprises applying a force between 1 Newton and 5 Newtons.

4. The method of claim 1, wherein a diameter of the first conductive member and the second conductive member is between 0.003 inches and 0.010 inches.

5. The method of claim 1, wherein applying pressure to the first conductive member and the second conductive member comprises clamping the first conductive member and the second conductive member.

6. The method of claim 1, wherein forming one or more electrical joints comprises soldering the first conductive member to the second conductive member.

7. The method of claim 1, wherein at least a portion of the second conductive member is coated or plated with a coating or plating comprising the first material.

8. The method of claim 1, wherein the first material comprises copper, and wherein the second material comprises molybdenum, tungsten, rhodium, rhenium, tantalum, niobium, or a combination thereof.

9. A method of forming a catheter comprising one or more electrical joints configured to electrically couple a first conductive member to a second conductive member, the method comprising:
- securing a first conductive member comprising a first material to a catheter body;
- securing a second conductive member comprising a second material different from the first material to the catheter body at a location distal of the first conductive member on the catheter body;
- flattening at least one of the first conductive member and the second conductive member; and
- forming one or more electrical joints for electrically coupling and joining the first conductive member and the second conductive member.

10. The method of claim 9, wherein, prior to flattening, a diameter of the first conductive member and the second conductive member is between 0.003 inches and 0.010 inches.

11. The method of claim 9, wherein at least a portion of the second conductive member is coated or plated with a coating or plating comprising the first material.

12. The method of claim 9, wherein the first material comprises copper, and wherein the second material comprises molybdenum, tungsten, rhodium, rhenium, tantalum, niobium, or a combination thereof.

13. A method of forming a catheter comprising one or more electrical joints configured to electrically couple a first conductive member to a second conductive member, the method comprising:
- securing a first conductive member comprising a first material to a catheter body;
- securing a second conductive member comprising a second material different from the first material to the catheter body at a location distal of the first conductive member on the catheter body;
- flowing an inert gas over at least a portion of the first conductive member and the second conductive member; and
- forming one or more electrical joints for electrically coupling and joining the first conductive member and the second conductive member.

14. The method of claim 13, comprising supplying the inert gas for between 1 and 10 seconds.

15. The method of claim 13, wherein a diameter of the first conductive member and the second conductive member is between 0.003 inches and 0.010 inches.

16. The method of claim 13, wherein at least a portion of the second conductive member is coated or plated with a coating or plating comprising the first material.

17. The method of claim 13, wherein the first material comprises copper, and wherein the second material comprises molybdenum, tungsten, rhodium, rhenium, tantalum, niobium, or a combination thereof.

18. A method of forming a catheter comprising one or more electrical joints configured to electrically couple a first conductive member to a second conductive member, the method comprising:
- securing a first conductive member comprising a first material to a catheter body;
- securing a second conductive member comprising a second material different from the first material to the catheter body at a location distal of the first conductive member on the catheter body; and
- forming one or more electrical joints for electrically coupling and joining the first conductive member and the second conductive member, wherein forming one or more electrical joints comprises:
- clamping the first conductive member and the second conductive member;
- heating the first conductive member and the second conductive member to melt at least one of the first conductive member and the second conductive member to join the first conductive member and the second conductive member together, wherein heating the first conductive member and the second conductive member comprises using a laser.

19. The method of claim 18, wherein the laser is pulsed for between 5 tenths of a millisecond and 15 milliseconds.

20. The method of claim 18, comprising: positioning the first conductive member and the second conductive member such that an end of the first conductive member contacts an end of the second conductive member.

21. The method of claim 20, wherein joining the first conductive member and the second conductive member together comprises:
- aligning a crosshair of the laser with the second conductive member;
- pulsing the laser to heat the second conductive member;
- aligning the crosshair of the laser with the first conductive member;
- pulsing the laser to melt the first conductive member; and
- pushing the first conductive member into the second conductive member to form an electrical joint of the one or more electrical joints.

22. The method of claim 21, wherein the first conductive member is pushed into the second conductive member such that the first conductive member and the second conductive member overlap by between 0.1 millimeters and 2.5 millimeters.

* * * * *